(12) United States Patent
Ferguson

(10) Patent No.: US 7,611,485 B2
(45) Date of Patent: *Nov. 3, 2009

(54) SAFETY SHIELD FOR MEDICAL NEEDLES

(75) Inventor: F. Mark Ferguson, Salt Lake City, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 596 days.

This patent is subject to a terminal disclaimer.

(21) Appl. No.: 10/919,983

(22) Filed: Aug. 17, 2004

(65) Prior Publication Data

US 2005/0043691 A1    Feb. 24, 2005

Related U.S. Application Data

(63) Continuation of application No. 10/202,201, filed on Jul. 23, 2002, now Pat. No. 6,902,546, which is a continuation-in-part of application No. 09/809,357, filed on Mar. 15, 2001, now Pat. No. 6,595,955.

(51) Int. Cl.
*A61M 5/00*   (2006.01)
*A61M 5/178*  (2006.01)
*A61M 5/32*   (2006.01)

(52) U.S. Cl. .................. 604/110; 604/263; 604/192; 604/164.08

(58) Field of Classification Search .......... 604/110, 604/263, 192–198, 163, 164.08
See application file for complete search history.

(56) References Cited

U.S. PATENT DOCUMENTS

| | | | |
|---|---|---|---|
| 1,436,707 A | 11/1922 | Gaschke | |
| 4,332,323 A | 6/1982 | Reenstierna | 206/365 |
| 4,373,526 A | 2/1983 | Kling | 128/215 |
| 4,425,120 A | 1/1984 | Sampson et al. | |
| 4,666,435 A | 5/1987 | Braginetz | |
| 4,762,516 A | 8/1988 | Luther | 605/164 |
| 4,790,828 A | 12/1988 | Dombrowski | 604/198 |
| 4,804,371 A | 2/1989 | Vaillancourt | 604/198 |
| 4,826,490 A | 5/1989 | Byrne | 604/198 |
| 4,832,696 A | 5/1989 | Luther | 604/164 |
| 4,834,718 A | 5/1989 | McDonald | 604/195 |
| 4,846,811 A | 7/1989 | Vanderhoof | 604/263 |

(Continued)

FOREIGN PATENT DOCUMENTS

DE    2133053    9/1994

(Continued)

OTHER PUBLICATIONS

Supplementary European Search Report dated Sep. 23, 2008.

(Continued)

*Primary Examiner*—Matthew F Desanto
(74) *Attorney, Agent, or Firm*—Rutan & Tucker LLP

(57) ABSTRACT

A medical needle shield apparatus is provided which is slidably movable along a medical needle from a proximal position where a distal end of the needle is exposed, to a distal position where the shield protects the distal end of the needle. The medical needle shield apparatus includes a binding member having an aperture through which the needle passes. The binding member also has binding surfaces for binding to a medical needle. The shield apparatus also includes a retainer integral with the binding member and in communication with the needle for temporarily retaining the binding surfaces in a non-binding position relative to the needle. The shield apparatus also includes a positioning member for positioning the binding surfaces to secure the shield to the needle when a portion of the retainer in contact with the needle is advanced past the distal end of the needle. A housing may be included for enclosing the shield apparatus.

30 Claims, 31 Drawing Sheets

U.S. PATENT DOCUMENTS

| | | | |
|---|---|---|---|
| 4,917,669 A | 4/1990 | Bonaldo | 604/164 |
| 4,929,241 A | 5/1990 | Kulli | 604/263 |
| 4,931,048 A | 6/1990 | Lopez | 604/110 |
| 4,944,725 A | 7/1990 | McDonald | 604/164 |
| 4,950,252 A | 8/1990 | Luther | 604/198 |
| 4,952,207 A | 8/1990 | Lemieux | 604/164 |
| 4,964,854 A | 10/1990 | Luther | 604/166 |
| 4,978,344 A | 12/1990 | Dombrowski | 604/198 |
| 4,994,041 A | 2/1991 | Dombrowski | 604/164 |
| 5,007,901 A | 4/1991 | Shields | 604/110 |
| 5,049,136 A | 9/1991 | Johnson | 604/198 |
| 5,051,109 A | 9/1991 | Simon | 604/263 |
| 5,053,017 A | 10/1991 | Chamuel | 604/192 |
| 5,059,180 A | 10/1991 | McLees | 604/110 |
| 5,084,023 A | 1/1992 | Lemieux | 604/167 |
| 5,084,030 A | 1/1992 | Byrne | 604/198 |
| 5,085,648 A | 2/1992 | Purdy | 604/198 |
| 5,127,905 A | 7/1992 | Lemieux | 604/164 |
| 5,135,504 A | 8/1992 | McLees | 604/164 |
| 5,147,327 A | 9/1992 | Johnson | 604/198 |
| 5,171,229 A | 12/1992 | McNeil | 604/192 |
| 5,183,468 A | 2/1993 | McLees | 604/164 |
| 5,205,829 A | 4/1993 | Lituchy | 604/164 |
| 5,215,528 A | 6/1993 | Purdy et al. | |
| 5,279,591 A | 1/1994 | Simon | |
| 5,300,045 A | 4/1994 | Plassche | 604/263 |
| 5,312,371 A | 5/1994 | Dombrowski | 604/198 |
| 5,313,958 A | 5/1994 | Bauer | |
| 5,322,517 A | 6/1994 | Sircom | 604/198 |
| 5,328,482 A | 7/1994 | Sircom et al. | |
| 5,334,158 A | 8/1994 | McLees | 604/110 |
| 5,342,310 A | 8/1994 | Ueyama | 604/110 |
| 5,344,408 A | 9/1994 | Partika | 604/192 |
| 5,348,544 A | 9/1994 | Sweeney | 604/192 |
| 5,411,486 A | 5/1995 | Zadini | 604/198 |
| 5,417,659 A | 5/1995 | Gaba | 604/110 |
| 5,419,766 A | 5/1995 | Chang | 604/110 |
| 5,423,766 A | 6/1995 | Di Cesare | 604/192 |
| 5,458,658 A | 10/1995 | Sircom | 604/192 |
| 5,478,313 A | 12/1995 | White | 604/110 |
| 5,487,733 A | 1/1996 | Caizza et al. | 604/164 |
| 5,531,704 A | 7/1996 | Knotek | 604/192 |
| 5,533,974 A | 7/1996 | Gaba | 604/110 |
| 5,538,508 A | 7/1996 | Steyn | 604/192 |
| 5,549,570 A | 8/1996 | Rogalsky | 604/198 |
| 5,558,651 A | 9/1996 | Crawford et al. | |
| 5,562,624 A | 10/1996 | Righi | 604/110 |
| 5,562,633 A | 10/1996 | Wozencroft | 604/171 |
| 5,582,597 A | 12/1996 | Brimhall et al. | 604/192 |
| 5,584,809 A | 12/1996 | Gaba | 604/110 |
| 5,584,810 A * | 12/1996 | Brimhall | 604/110 |
| 5,584,818 A | 12/1996 | Morrison | 604/197 |
| 5,595,566 A | 1/1997 | Vallelunga et al. | |
| 5,599,310 A | 2/1997 | Bogert | 604/164 |
| 5,601,532 A | 2/1997 | Gaba | 604/110 |
| 5,601,536 A | 2/1997 | Crawford | 604/263 |
| 5,611,781 A | 3/1997 | Sircom | 604/164 |
| 5,662,610 A | 9/1997 | Sircom | 604/110 |
| 5,683,365 A | 11/1997 | Brown | 604/110 |
| 5,697,907 A | 12/1997 | Gaba | 604/110 |
| 5,718,688 A | 2/1998 | Wozencroft | 604/164 |
| 5,725,504 A | 3/1998 | Collins | 604/165 |
| 5,735,827 A | 4/1998 | Adwers et al. | |
| 5,738,665 A | 4/1998 | Caizza et al. | |
| 5,749,856 A | 5/1998 | Zadini | 604/162 |
| 5,853,393 A | 12/1998 | Bogert | 604/165 |
| 5,879,337 A | 3/1999 | Kuracina | 604/192 |
| 5,882,337 A | 3/1999 | Bogert et al. | |
| 5,910,130 A | 6/1999 | Caizza et al. | 604/110 |
| 5,911,705 A | 6/1999 | Howell | 604/110 |
| 5,919,168 A | 7/1999 | Wheeler | |
| 5,938,641 A | 8/1999 | Villanueva | |
| 5,947,936 A | 9/1999 | Bonds | |
| 5,951,515 A | 9/1999 | Osterlind | 604/110 |
| 5,951,523 A | 9/1999 | Osterlind et al. | |
| 5,964,731 A | 10/1999 | Kovelman | |
| 5,980,488 A | 11/1999 | Thorne | 604/110 |
| 6,001,080 A | 12/1999 | Kuracina | 604/171 |
| 6,004,294 A | 12/1999 | Brimhall et al. | |
| 6,010,487 A | 1/2000 | DeMichele et al. | |
| 6,015,397 A | 1/2000 | Elson et al. | |
| 6,022,366 A | 2/2000 | Schraga | |
| 6,117,108 A | 9/2000 | Woehr et al. | |
| 6,132,401 A | 10/2000 | Van Der Meyden | 604/195 |
| 6,193,694 B1 | 2/2001 | Bell et al. | 604/192 |
| 6,203,527 B1 | 3/2001 | Zadini | 604/110 |
| 6,210,373 B1 | 4/2001 | Allmon | 604/192 |
| 6,221,047 B1 | 4/2001 | Green et al. | 604/164 |
| 6,254,575 B1 | 7/2001 | Phillips | |
| 6,280,419 B1 | 8/2001 | Vojtasek | 604/192 |
| 6,287,278 B1 | 9/2001 | Woehr et al. | 604/110 |
| 6,406,459 B1 | 6/2002 | Allmon | 604/192 |
| 6,443,927 B1 | 9/2002 | Cook | 604/110 |
| 6,443,929 B1 | 9/2002 | Kuracina et al. | 604/192 |
| 6,585,704 B2 | 7/2003 | Luther et al. | 604/263 |
| 6,595,955 B2 | 7/2003 | Ferguson et al. | |
| 6,616,630 B1 * | 9/2003 | Woehr et al. | 604/110 |
| 6,623,458 B2 | 9/2003 | Woehr et al. | 604/192 |
| 6,629,959 B2 | 10/2003 | Kuracina et al. | 604/192 |
| 6,652,486 B2 | 11/2003 | Bialecki et al. | |
| 6,652,490 B2 | 11/2003 | Howell | |
| 6,682,510 B2 | 1/2004 | Niermann | 604/263 |
| 6,689,102 B2 | 2/2004 | Greene | |
| 6,695,814 B2 | 2/2004 | Greene et al. | |
| 6,796,962 B2 | 9/2004 | Ferguson et al. | |
| 6,816,630 B1 | 11/2004 | Werth et al. | |
| 6,902,546 B2 | 6/2005 | Ferguson | |
| 6,984,213 B2 | 1/2006 | Saito | |
| 7,004,927 B2 | 2/2006 | Ferguson et al. | |
| 7,008,402 B2 | 3/2006 | Ferguson et al. | |
| 7,179,244 B2 | 2/2007 | Smith et al. | |
| 7,341,573 B2 | 3/2008 | Ferguson et al. | |
| 7,357,784 B2 | 4/2008 | Ferguson | |
| 7,413,562 B2 | 8/2008 | Ferguson et al. | |
| 7,458,954 B2 | 12/2008 | Ferguson et al. | |
| 2002/0099339 A1 | 7/2002 | Niermann | 604/263 |
| 2002/0107463 A1 | 8/2002 | Cook | 604/164.01 |
| 2002/0133122 A1 | 9/2002 | Giambattista et al. | |
| 2002/0151850 A1 | 10/2002 | Ferguson et al. | |
| 2002/0177813 A1 | 11/2002 | Adams et al. | 604/164.07 |
| 2002/0177818 A1 | 11/2002 | Vaillancourt | 604/198 |
| 2002/0193745 A1 | 12/2002 | Ferguson | |
| 2003/0036731 A1 | 2/2003 | Wilkinson et al. | 604/198 |
| 2003/0100868 A1 | 5/2003 | Ferguson et al. | |
| 2003/0114797 A1 | 6/2003 | Vaillancourt et al. | 604/171 |
| 2003/0135157 A1 | 7/2003 | Saulenas et al. | 604/110 |
| 2003/0144627 A1 | 7/2003 | Woehr et al. | 604/110 |
| 2003/0181875 A1 | 9/2003 | Bressler et al. | |
| 2003/0195471 A1 | 10/2003 | Woehr et al. | 604/164.08 |
| 2003/0195475 A1 | 10/2003 | Ferguson et al. | |
| 2003/0195479 A1 | 10/2003 | Kuracina et al. | 604/263 |
| 2003/0199827 A1 | 10/2003 | Thorne | |
| 2003/0216687 A1 | 11/2003 | Hwang | 604/110 |
| 2004/0010227 A1 | 1/2004 | Riesenberger et al. | 604/110 |
| 2004/0049155 A1 | 3/2004 | Schramm | |
| 2004/0049163 A1 | 3/2004 | Murashita | |
| 2004/0078003 A1 | 4/2004 | Smith et al. | |
| 2004/0092888 A1 | 5/2004 | Ferguson | |
| 2004/0092889 A1 | 5/2004 | Ferguson | |
| 2004/0111057 A1 | 6/2004 | Wilkinson | |
| 2004/0133167 A1 | 7/2004 | Ferguson et al. | |
| 2004/0171989 A1 | 9/2004 | Horner et al. | |
| 2004/0171995 A1 | 9/2004 | Niermann | 604/263 |
| 2004/0181173 A1 | 9/2004 | Wilkinson | 600/576 |

| | | | |
|---|---|---|---|
| 2004/0215154 | A1 | 10/2004 | Hwang et al. |
| 2004/0236289 | A1 | 11/2004 | Ferguson et al. |
| 2005/0043691 | A1 | 2/2005 | Ferguson |
| 2005/0059937 | A1 | 3/2005 | Ferguson |
| 2005/0070855 | A1 | 3/2005 | Ferguson et al. |
| 2005/0096592 | A1 | 5/2005 | Carlyon et al. |
| 2007/0083167 | A1 | 4/2007 | Smith et al. |
| 2007/0106231 | A1 | 5/2007 | Snow et al. |
| 2008/0097345 | A1 | 4/2008 | Ferguson |
| 2009/0038135 | A1 | 2/2009 | Snow et al. |
| 2009/0043262 | A1 | 2/2009 | Snow |
| 2009/0048566 | A1 | 2/2009 | Ferguson et al. |

FOREIGN PATENT DOCUMENTS

| | | |
|---|---|---|
| DE | 4434569 | 3/1995 |
| EP | 0 702 972 B1 | 7/1995 |
| EP | 07509158 | 6/1996 |
| EP | 0 750 915 A2 | 1/1997 |
| EP | 1 027 903 A1 | 8/2000 |
| EP | 1 110 571 A1 | 6/2001 |
| EP | 1 112 754 A1 | 7/2001 |
| EP | 1 374 772 A1 | 1/2004 |
| JP | H04-504512 | 8/1992 |
| JP | H05-345032 | 12/1993 |
| JP | H07-148176 | 6/1995 |
| JP | H09-028801 | 2/1997 |
| JP | H09-099068 | 4/1997 |
| WO | WO 90/08564 | 8/1990 |
| WO | WO97/42989 | 5/1997 |
| WO | WO 97/42989 | 11/1997 |
| WO | WO99/08742 | 8/1998 |
| WO | WO 99/08742 | 8/1998 |
| WO | WO 01/10488 A1 | 2/2001 |
| WO | WO 01/56642 | 8/2001 |
| WO | WO 02/45786 A2 | 6/2002 |
| WO | WO 02/076526 | 10/2002 |
| WO | WO 03/103757 A1 | 12/2003 |
| WO | WO 2004/014464 | 2/2004 |
| WO | WO 2004/043551 | 5/2004 |
| WO | WO2004/060138 | 7/2004 |
| WO | WO 2004/091687 | 10/2004 |
| WO | WO 2005/053774 | 6/2005 |
| WO | WO 2005/072621 | 8/2005 |
| WO | WO 2006/113542 | 10/2006 |
| WO | WO 2006/113675 | 10/2006 |

OTHER PUBLICATIONS

Response to Office Action dated Dec. 27, 2002 in U.S. Appl. No. 09/809,357 (6,595,955).
Office Action dated Sep. 27, 2002 dated in U.S. Appl. No. 09/809,357 (6,595,955).
Advisory Action dated Sep. 17, 2004 in U.S. Appl. No. 10/202,201 (6,902,546).
Response to Office Action dated Aug. 16, 2004 in U.S. Appl. No. 10/202,201 (6,902,546).
Office Action dated May 17, 2004 in U.S. Appl. No. 10/202,201 (6,902,546).
Response to Office Action dated Feb. 03, 2004 in U.S. Appl. No. 10/202,201 (6,902,546).
Office Action dated Dec. 29, 2003 in U.S. Appl. No. 10/202,201 (6,902,546).
Terminal Disclaimer dated Jan. 16, 2008 in U.S. Appl. No. 10/984,342 (7,357,784).
Terminal Disclaimer dated Dec. 19, 2007 in U.S. Appl. No. 10/984,342 (7,357,784).
Response to Office Action dated Dec. 19, 2007 in U.S. Appl. No. 10/984,342 (7,357,784).
Office Action dated Sep. 12, 2007 in U.S. Appl. No. 10/984,342 (7,357,784).
Preliminary Amendment dated Jun. 06, 2005 in U.S. Appl. No. 10/984,342 (7,357,784).
Office Action dated Oct. 17, 2006 in U.S. Appl. No. 10/739,868 (7,413,562).
Response to Office Action dated Sep. 28, 2006 in U.S. Appl. No. 10/739,868 (7,413,562).
Office Action dated Jun. 28, 2006 in U.S. Appl. No. 10/739,868 (7,413,562).
Preliminary Amendment dated May 24, 2004 in U.S. Appl. No. 10/739,868 (7,413,562).
Examiner's Amendment dated Aug. 29, 2005 in U.S. Appl. No. 10/766,369 (6,984,213).
Response to Office Action dated Aug. 05, 2005 in U.S. Appl. No. 10/766,369 (6,984,213).
Office Action dated Jun. 23, 2005 in U.S. Appl. No. 10/766,369 (6,984,213).
Preliminary Amendment dated Jun. 01, 2004 in U.S. Appl. No. 10/766,369 (6,984,213).
Response to Office Action dated May 11, 2007 in U.S. Appl. No. 10/877,725 (7,341,573).
Office Action dated Nov. 14, 2006 in U.S. Appl. No. 10/766,369 (6,984,213).
Drawing dated Oct. 4, 2004 in U.S. Appl. No. 10/766,369 (6,984,213).
Preliminary Amendment dated Oct. 4, 2004 in U.S. Appl. No. 10/766,369 (6,984,213).
Examiner's Amendment dated Nov. 22, 2005 in U.S. Appl. No. 10/454,228 (7,008,402).
Terminal Disclaimer dated Mar. 4, 2008 in U.S. Appl. No. 10/660,083 (7,458,954).
Response to Office Action dated Mar. 4, 2008 in U.S. Appl. No. 10/660,083 (7,458,954).
Office Action dated Jan. 22, 2008 in U.S. Appl. No. 10/660,083 (7,458,954).
Ex Parte Quayle Action dated Aug. 1, 2007 in U.S. Appl. No. 10/660,083 (7,458,954).
Office Action dated Sep. 24, 2002 for U.S. Appl. No. 09/809,357.
Notice of Allowance dated Mar. 21, 2003 for U.S. Appl. No. 09/809,357.
Office Action dated May 17, 2004 for U.S. Appl. No. 10/202,201.
Interview Summary dated Jul. 13, 2004 for U.S. Appl. No. 10/202,201.
Response to Office Action dated Jul. 13, 2004 for U.S. Appl. No. 10/202,201.
Interview Summary dated Aug. 13, 2004 for U.S. Appl. No. 10/202,201.
Notice of Allowance dated Oct. 20, 2004 for U.S. Appl. No. 10/202,201.
Office Action dated Oct. 28, 2003 for U.S. Appl. No. 10/202,201.
Response to Office Action dated Nov. 10, 2003 for U.S. Appl. No. 10/202,201.
Request for Continued Examination dated Jan. 07, 2009 for U.S. Appl. No. 11/958,204.
Notice of Allowance dated Jan. 08, 2008 for U.S. Appl. No. 11/958,204.
Notice of Allowance dated Jan. 27, 2009 for U.S. Appl. No. 11/958,204.
Notice of Allowance dated Apr. 17, 2009 for U.S. Appl. No. 11/958,204.
Terminal Disclaimer dated Jan. 16, 2008 for U.S. Appl. No. 10/984,342.
Notice of Allowance dated Feb. 12, 2008 for U.S. Appl. No. 10/984,342.
Interview Summary dated Nov. 27, 2007 for U.S. Appl. No. 10/984,342.
Notice of Allowance dated Jan. 18, 2005 for U.S. Appl. No. 10/322,288.
Office Action dated Jan. 27, 2004 for U.S. Appl. No. 10/322,288.
Response to Office Action dated 02117/2004 for U.S. Appl. No. 10/322,288.
Office Action dated May 14, 2004 for U.S. Appl. No. 10/322,288.
Interview Summary dated Jul. 13, 2004 for U.S. Appl. No. 10/322,288.
Office Action dated Aug. 13, 2004 for U.S. Appl. No. 10/322,288.

Response to Office Action dated Aug. 16, 2004 for U.S. Appl. No. 10/322,288.
Office Action dated Oct. 25, 2004 for U.S. Appl. No. 10/322,288.
Interview Summary dated Dec. 16, 2004 for U.S. Appl. No. 10/322,288.
Response to Office Action dated Dec. 21, 2004 for U.S. Appl. No. 10/322,288.
Interview Summary dated Dec. 29, 2004 for U.S. Appl. No. 10/322,288.
Notice of Abandonment dated Apr. 30, 2008 for U.S. Application No. 10/984,268.
Office Action dated Sep. 11, 2007 for U.S. Appl. No. 10/984,268.
Office Action dated Jan. 21, 2004 for U.S. Appl. No. 10/409,819.
Response to Office Action dated Feb. 2, 2004 for U.S. Appl. No. 10/409,819.
Office Action dated Mar. 5, 2004 for U.S. Appl. No. 10/409,819.
Response to Office Action dated Mar. 22, 2004 for U.S. Appl. No. 10/409,819.
Notice of Allowance dated Jun. 09, 2004 for U.S. Appl. No. 10/409,819.
Office Action dated Mar. 07, 2005 for U.S. Appl. No. 10/721,526.
Response to Office Action dated Apr. 04, 2005 for U.S. Appl. No. 10/721,526.
Office Action dated Jun. 10, 2005 for U.S. Appl. No. 10/721,526.
Response to Office Action dated Jul. 14, 2005 for U.S. Appl. No. 10/721,526.
Interview Summary dated Aug. 15, 2005 for U.S. Appl. No. 10/721,526.
Office Action dated Sep. 14, 2005 for U.S. Appl. No. 10/721,526.
Petition Decision dated Oct. 2, 2006 for U.S. Application No. 10/721,526.
Response to Office Action dated Nov. 14, 2005 for U.S. Appl. No. 10/721,526.
Notice of Allowance dated Nov. 21, 2006 for U.S. Appl. No. 10/721,526.
Notice of Allowance dated Nov. 30, 2005 for U.S. Appl. No. 10/721,526.
Office Action dated Dec. 29, 2008 for U.S. Appl. No. 11/635,879.
Response to Office Action dated Mar. 02, 2009 for U.S. Appl. No. 10/580,878.
Office Action dated Apr. 08, 2009 for U.S. Appl. No. 10/580,878.
Preliminary Amendment dated Apr. 12, 2007 for U.S. Appl. No. 10/580,878.
Preliminary Amendment dated May 25, 2006 for U.S. Appl. No. 10/580,878.
Office Action dated Jul. 31, 2008 for U.S. Appl. No. 10/580,878.
Response to Office Action dated Sep. 02, 2008 for U.S. Appl. No. 10/580,878.
Office Action dated Nov. 03, 2008 for U.S. Appl. No. 10/580,878.
Office Action dated Feb. 12, 2007 for U.S. Appl. No. 10/739,868.
Response to Office Action dated Feb. 25, 2008 for U.S. Appl. No. 10/739,868.
Notice of Allowance dated Apr. 10, 2008 for U.S. Appl. No. 10/739,868.
Interview Summary dated May 3, 2007 for U.S. Appl. No. 10/739,868.
Response to Office Action dated Aug. 13, 2007 for U.S. Appl. No. 10/739,868.
Office Action dated Aug. 24, 2007 for U.S. Application No. 10/739,868.
Request for Continued Examination and Response to Office Action dated Nov. 1, 2007 for U.S. Appl. No. 10/739,868.
Interview Summary dated Nov. 20, 2007 for U.S. Appl. No. 10/739,868.
Request for Continued Examination and Response to Office Action dated Dec. 22, 2006 for U.S. Appl. No. 10/739,868.
Notice of Allowance dated Aug. 29, 2005 for U.S. Appl. No. 10/766,369.
Notice of Allowance dated Oct. 9, 2007 for U.S. Appl. No. 10/877,725.
Interview Summary dated Nov. 29, 2006 for U.S. Appl. No. 10/877,725.
Office Action dated Aug. 15, 2005 for U.S. Appl. No. 10/454,228.
Response to Office Action dated Sep. 6, 2005 for U.S. Appl. No. 10/454,228.
Preliminary Amendment dated Jan. 24, 2005 for U.S. Appl. No. 10/660,083.
Office Action dated Feb. 5, 2007 for U.S. Appl. No. 10/660,083.
Response to Office Action dated May 8, 2007 for U.S. Appl. No. 10/660,083.
Terminal Disclaimers dated May 8, 2007 for U.S. Appl. No. 10/660,083.
Office Action dated Jun. 9, 2006 for U.S. Appl. No. 10/660,083.
Response to Office Action dated Jul. 3, 2006 for U.S. Appl. No. 10/660,083.
Notice of Allowance dated Aug. 25, 2008 for U.S. Appl. No. 10/660,083.
Office Action dated Aug. 31, 2006 for U.S. Appl. No. 10/660,083.
Request for Continued Examination and Response to Office Action dated Nov. 1, 2007 for U.S. Appl. No. 10/660,083.
Response to Office Action dated Nov. 22, 2006 for U.S. Appl. No. 10/660,083.
Interview Summary dated Dec. 15, 2006 for U.S. Appl. No. 10/660,083.
International Preliminary Examination Report dated Dec. 16, 2004 in International Application No. PCT/US03/22093, which published as WO 2004/014464.
International Preliminary Examination Report dated Apr. 26, 2005 in International Application No. PCT/US03/38340, which published as WO 2004/060138.
International Search Report dated Jun. 18, 2004 in International Application No. PCT/US03/38340, which published as WO 2004/060138.
International Preliminary Report on Patentability dated Apr. 30, 2007 in International Application No. PCT/US2006/14260, which published as WO 2006/113542.
Written Opinion of the International Searching Authority dated Jul. 06, 2006 in International Application No. PCT/US2006/14260, which published as WO 2006/113542.
International Search Report dated Sep. 22, 2008 in International Application No. PCT/US2006/014497, which published as WO 2006/113675.
Revised International Search Report dated Nov. 14, 2008 in International Application No. PCT/US2006/014497, which published as WO 2006/113675.
Written Opinion of the International Searching Authority dated Sep. 10, 2008 in International Application No. PCT/US2006/014497, which published as WO 2006/113675.
Corrected Opinion of the International Searching Authority dated Nov. 14, 2008 in International Application No. PCT/US2006/014497, which published as WO 2006/113675.
International Preliminary Report on Patentability dated Jul. 21, 2005 in International Application No. PCT/USO4/39400, which published as WO 2005/053774.
Written Opinion of the International Searching Authority dated Apr. 07, 2005 in International Application No. PCT/USO4/39400, which published as WO 2005/053774.
International Preliminary Report on Patentability dated May 23, 2006 in International Application No. PCT/US05/01345, which published as WO 2005/072621.
Written Opinion of the International Searching Authority dated Jul. 8, 2005 International Application No. PCT/US05/01345, which published as WO 2005/072621.
International Preliminary Report on Patentability dated Jan. 12, 2005 in International Application No. PCT/USO4/10800, which published as WO 2004/091687.

Written Opinion of the International Searching Authority dated Oct. 13, 2004 in International Application No, PCT/USO4/10800, which published as WO 2004/091687.

International Search Report dated Oct. 13, 2004 in International Application No. PCT/USO4/10800, which published as WO 2004/091687.

International Preliminary Examination Report dated Jun. 23, 2004 in International Application No. PCT/US03/32577, which published as WO 2004/043521.

International Preliminary Examination Report dated Nov. 17, 2003 in International Application No. PCT/US02106600, which published as WO 2002/076526.

International Search Report dated Sep. 5, 2002 in International Application No. PCT/US02/06600, which published as WO 2002/076526.

* cited by examiner

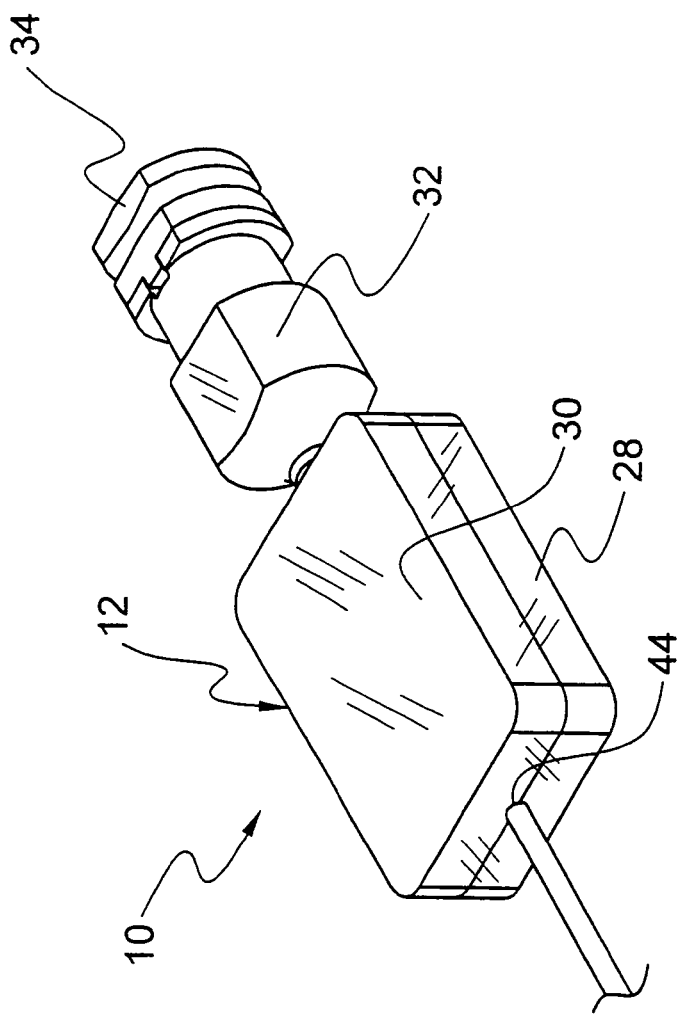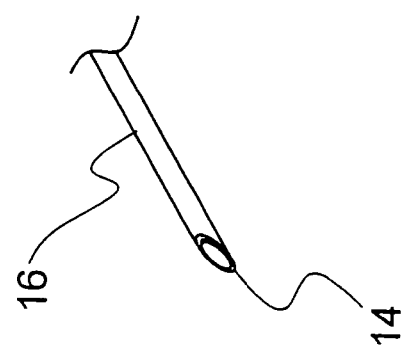
FIGURE 1

SAFETY SHIELD FOR MEDICAL NEEDLES

CROSS-REFERENCE TO RELATED APPLICATIONS

This patent application is a Continuation of application Ser. No. 10/202,201 filed in the U.S. Patent and Trademark Office on Jul. 23, 2002, now U.S. Pat. No. 6,902,546 which is a continuation-in-part of U.S. patent application Ser. No. 09/809,357, filed in the U.S. Patent and Trademark Office on Mar. 15, 2001 now U.S. Pat. No. 6,595,955 by Ferguson et al., the entire contents of each of these disclosures being hereby incorporated by reference herein.

BACKGROUND

1. Technical Field

The present disclosure generally relates to safety shields for medical needles, and more particularly, to safety shields that protect a needle point of a medical needle.

2. Description of the Related Art

Problems associated with inadvertent needle sticks are well known in the art of blood sampling, percutaneous medication injection and other medical procedures involving use of medical needles. Significant attention has been focused on needle stick problems due to the contemporary sensitivity of exposure to AIDS, Hepatitis and other serious blood-borne pathogen exposures.

Procedures for removing a needle from a patient commonly require a technician to use one hand to place pressure at the wound site where the needle is being withdrawn, while removing the needle device with the other hand. It is also common practice for an attending technician to give higher priority to care for the wound than is given to disposal of a needle. In the case of typical needle devices without safety shields, such priority either requires the convenience of an available sharps container within reach or another means for safe disposal without leaving the patient's side. Providing adequate care while following safety procedures is often compounded by the patient's physical condition and mental state, such as in burn units and psychiatric wards. Under such conditions, it is difficult to properly dispose of a used needle while caring for a patient.

The widespread knowledge and history associated with needle care and disposal problems have resulted in numerous devices for preventing accidental needle sticks. Problems of current safety devices include difficulty of use and high cost due to their complexity and number of parts.

Other known devices employ sheaths that are spring activated, telescoping, pivoting, etc. These devices, however, may disadvantageously misfire or be cumbersome to activate. Further drawbacks of current devices include high manufacturing cost due to complexity and the number of parts. Thus, these type prior art devices may not adequately and reliably shield medical needle apparatus to prevent hazardous exposure.

Consequently, there remains a need to provide a more satisfactory solution for needle safety devices by overcoming the disadvantages and drawbacks of the prior art. Therefore, it would be desirable to provide a more adequate and reliable medical needle shield apparatus which employs a safety shield slidably movable along a medical needle to prevent hazardous exposure to a needle tip. Such a needle shield apparatus should be easily and reliably movable to shield a needle tip of a needle cannula.

SUMMARY

Accordingly, the present disclosure addresses a need for a medical needle shield apparatus which effectively and inexpensively protects a tip of a medical needle after use. The present disclosure resolves related disadvantages and drawbacks experienced in the art. More specifically, the apparatus and method of this invention constitute an important advance in the art of safety needle devices.

In one particular embodiment, a medical needle shield apparatus is provided in accordance with the principles of the present disclosure. The shield is slidably movable along a medical needle from a proximal position where a distal end of the needle is exposed, to a distal position where the shield protects the distal end of the needle. The medical needle shield apparatus includes a binding member having an aperture through which the needle passes. The binding member also has binding surfaces for binding to a medical needle. The shield apparatus also includes a retainer integral with the binding member and in communication with the needle for temporarily retaining the binding surfaces in a non-binding position relative to the needle. The shield apparatus also includes a positioning member for positioning the binding surfaces to secure the shield to the needle when a portion of the retainer in contact with the needle is advanced past the distal end of the needle and allows the retainer to release from the needle and move out of an axial path defined by the needle. The retainer may also be configured so that it does not move out of an axial path defined by the needle. A housing may be included for enclosing the shield apparatus.

In one particular embodiment, the shield apparatus includes a positioning member comprising a leaf spring integral to the binding member. Alternatively, the positioning member may comprise one or more friction elements disposed on the medical needle. In another particular embodiment, the positioning member comprises a unitary friction element disposed on the medical needle.

In another particular embodiment, the shield apparatus includes a retainer having a slot for permitting a guidewire to extend through the safety shield apparatus.

BRIEF DESCRIPTION OF THE DRAWINGS

The foregoing and other features and advantages of the present invention will be more fully understood from the following detailed description of the illustrative embodiments, taken in conjunction with the accompanying drawings in which:

FIG. 1 is a perspective view of a medical needle safety shield apparatus in a retracted position, in accordance with the principles of the present invention;

FIG. 28 is a side view of the safety shield apparatus shown in FIG. 23 with the top portion of the housing removed and showing the alternate retainer embodiment illustrated in FIG. 27 providing for a guidewire to pass through;

DETAILED DESCRIPTION OF THE EXEMPLARY EMBODIMENTS

Figure 2:
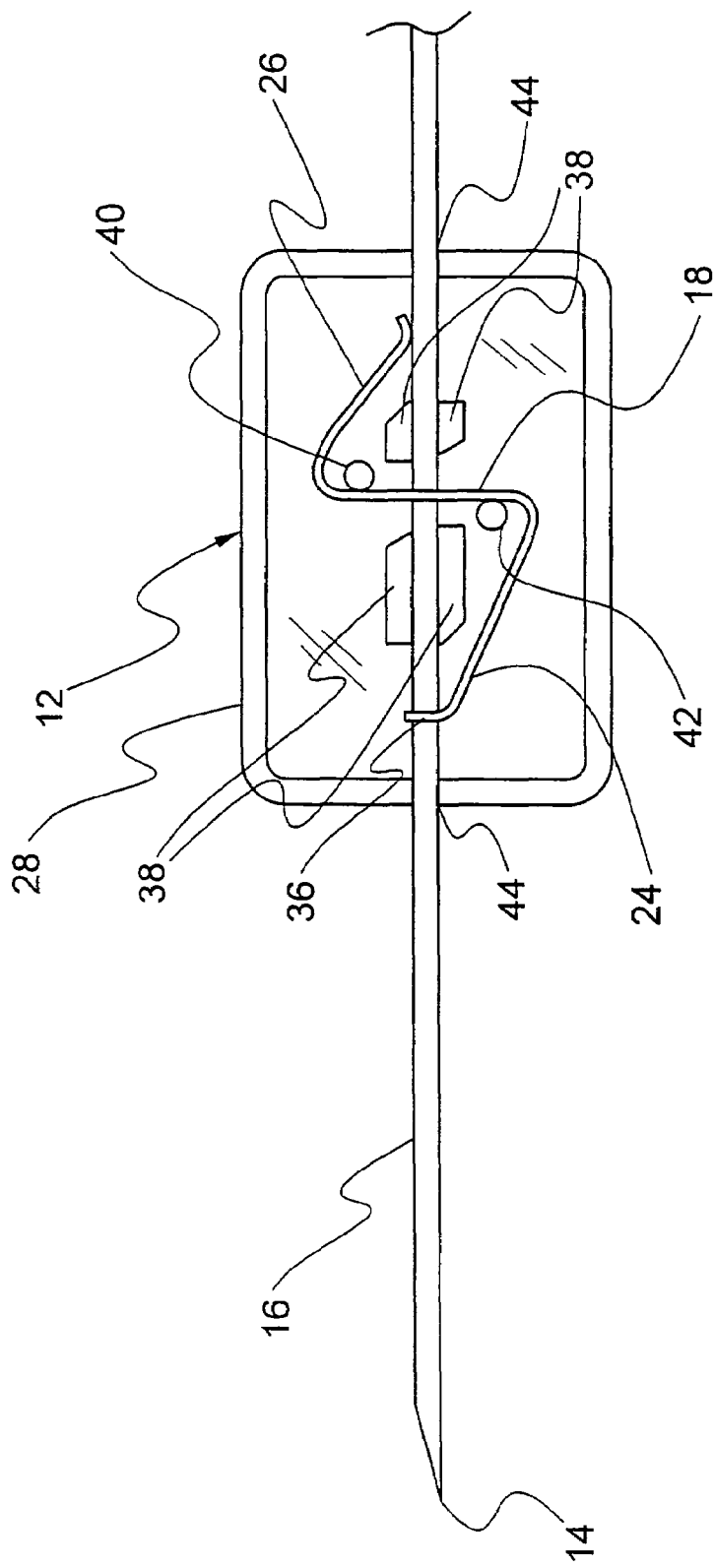
FIG. 2 is a side view of the safety shield apparatus shown in FIG. 1 with the top portion of the housing of the medical needle safety apparatus removed.
Figure 3:
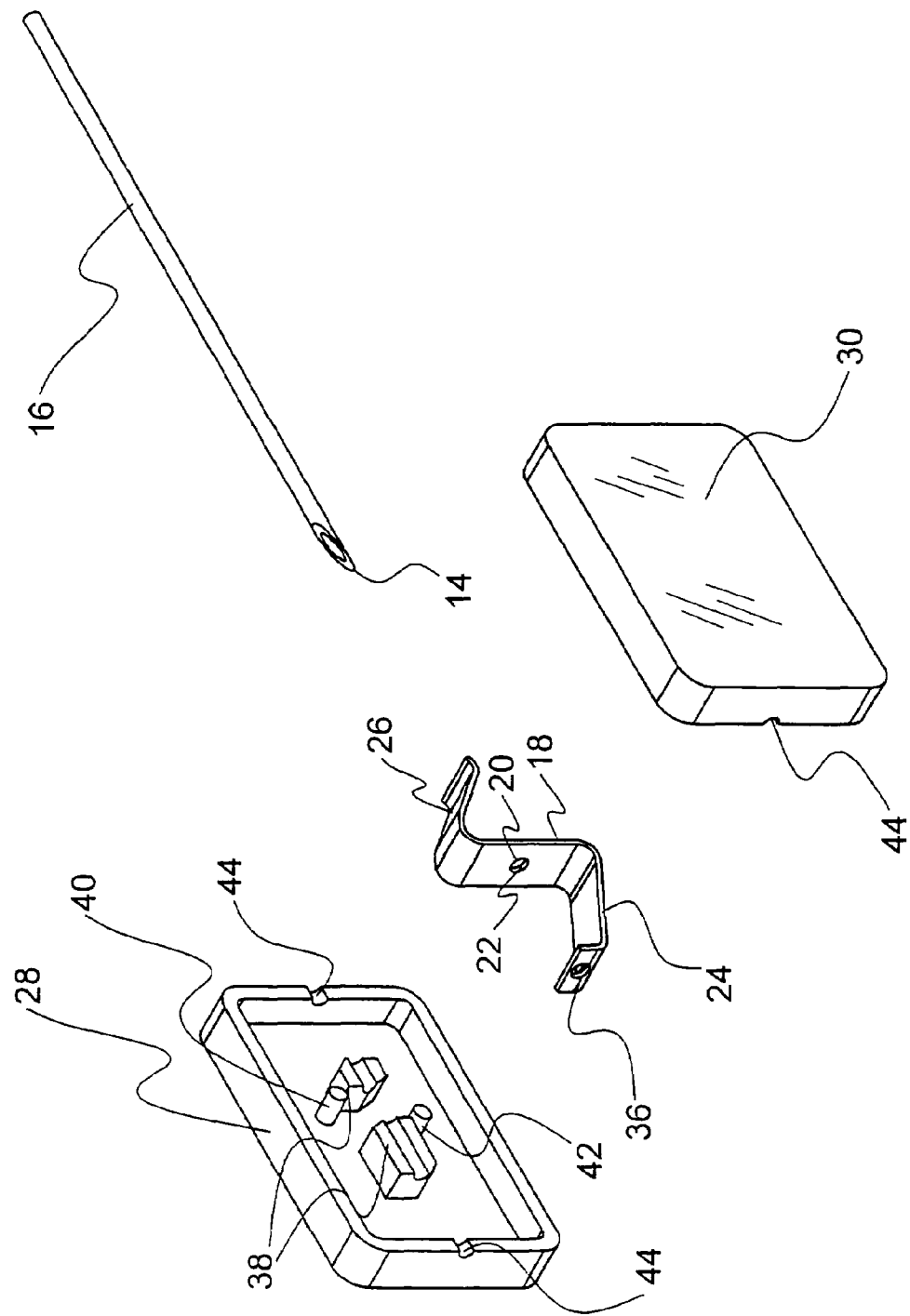
FIG. 3 is a perspective view of the safety shield apparatus illustrated in FIG. 1 with the components separated.
Figure 4:
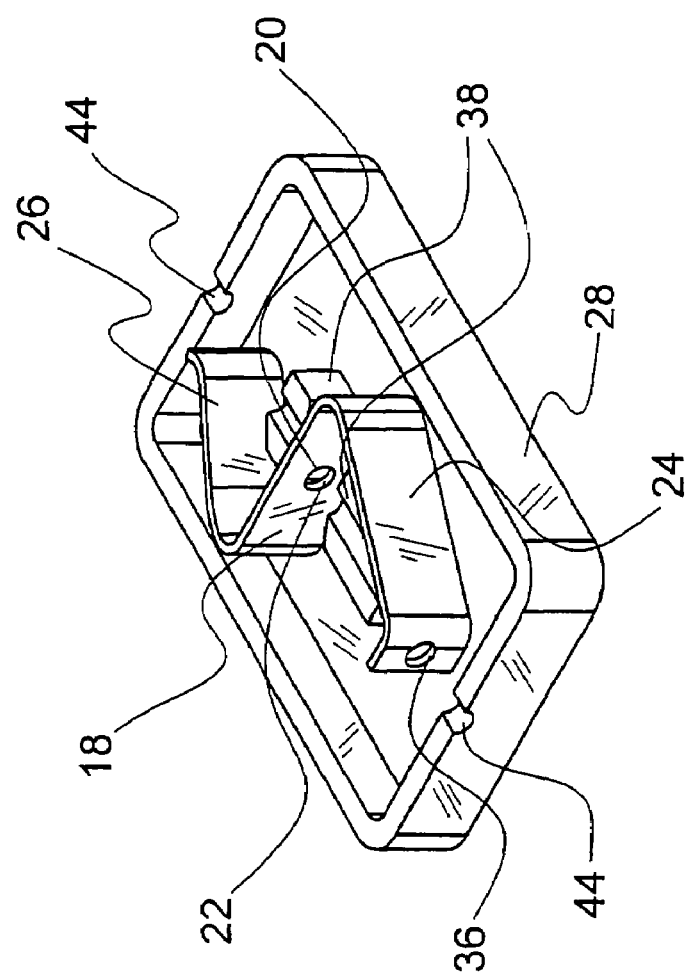
FIG. 4 is a perspective view of a portion of the components of the safety shield apparatus shown in FIG. 1.
Figure 5:
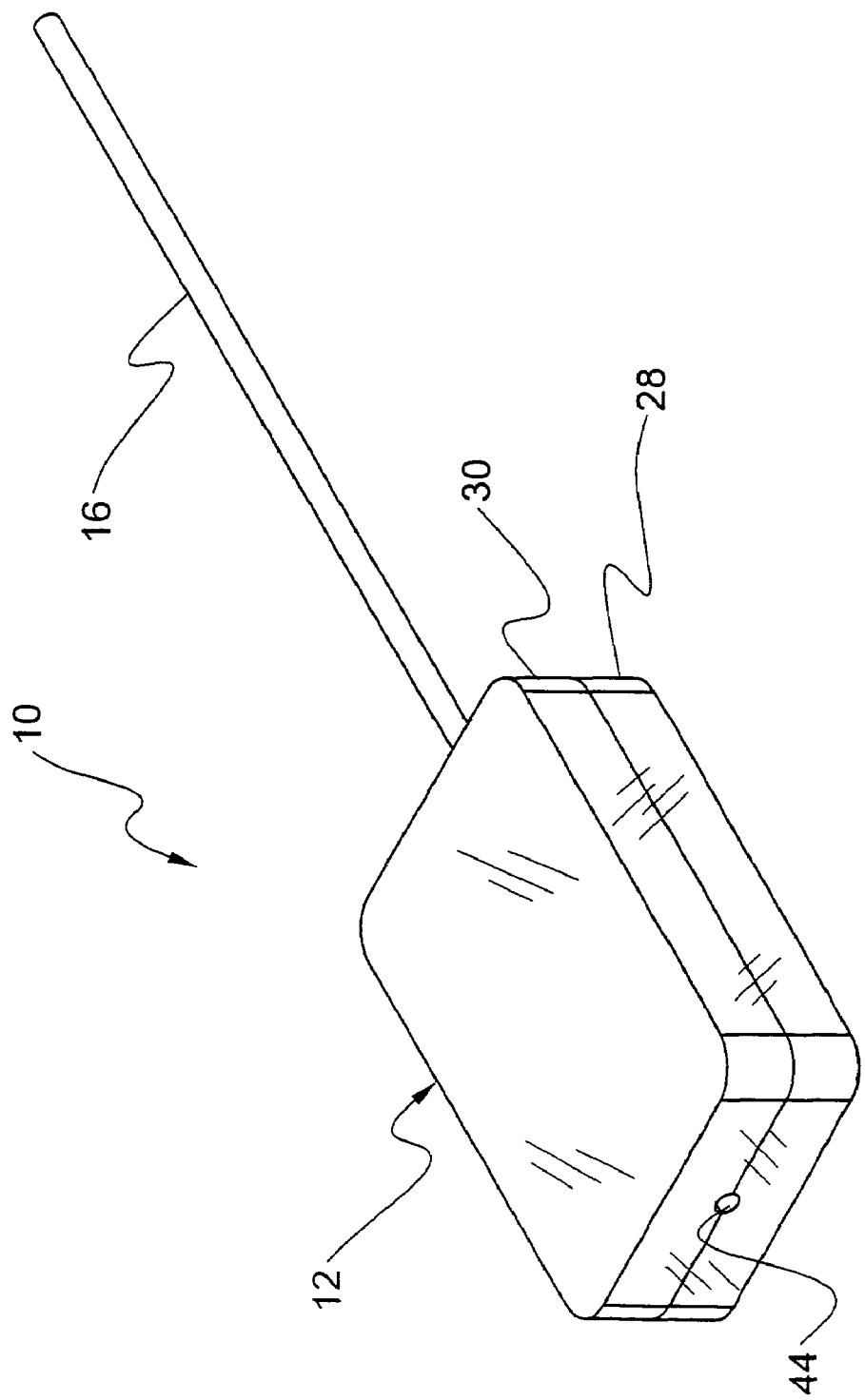
FIG. 5 is a perspective view of the safety shield apparatus illustrated in FIG. 1 fully extended.

The exemplary embodiments of the medical needle shield apparatus and methods of operation disclosed are discussed in terms of medical needles for infusion of intravenous fluids, medication infusion or fluid collection, and more particularly, in terms of needle shield apparatus employed with a needle cannula that prevent hazardous exposure to the needle tip, including, for example, inadvertent needle sticks. It is envisioned that the present disclosure, however, finds application to a wide variety of cannula needles and devices for the infusion of preventive medications, medicaments, therapeutics, etc. to a subject. It is also envisioned that the present disclosure may be employed for collection of body fluids including those employed during procedures relating to phlebotomy, digestive, intestinal, urinary, veterinary, etc. It is contemplated that the medical needle shield apparatus may be utilized with other medical needle applications including, but not limited to, fluid infusion, fluid collection, catheters, catheter introducers, guidewire introducers, spinal and epidural, biopsy, aphaeresis, dialysis, blood donor, Veress needles, Huber needles, etc.

In the discussion that follows, the term "proximal" refers to a portion of a structure that is closer to a clinician, and the term "distal" refers to a portion that is further from the clinician. As used herein, the term "subject" refers to a patient that receives infusions or has blood and/or fluid collected therefrom using the medical needle shield apparatus. According to the present disclosure, the term "clinician" refers to an individual administering an infusion, performing fluid collection, installing or removing a needle cannula from a medical needle shield apparatus and may include support personnel.

The following discussion includes a description of the medical needle shield apparatus, followed by a description of the method of operating the medical needle shield apparatus in accordance with the present disclosure. Reference will now be made in detail to the exemplary embodiments of the disclosure, which are illustrated in the accompanying figures.

Turning now to the figures, wherein like components are designated by like reference numerals throughout the several views. Referring initially to FIGS. 1-7, there is illustrated a safety shield assembly 10, constructed in accordance with the principals of the present disclosure, including a needle, such as, for example, medical needle 16 having a distal end 14. Safety shield assembly 10 is advantageously configured to prevent hazardous exposure to the distal end 14 of a needle cannula 16 by providing an adequate and reliable medical needle shield apparatus for a medical needle 16 which shields the distal end 14 of a needle 16, as will be discussed below.

Safety shield assembly 10 may include a housing 12 having a first section 28 and second section 30 for ease of assembly. Housing 12 includes openings 44 sized to allow the needle 16 to pass through. Safety shield 10 is disposed on a needle 16 of a medical needle device to facilitate safe disposal of a medical needle device. FIG. 1 illustrates safety shield assembly 10 disposed near the hub 32 of on a needle having a stylet 34.

Safety shield 10 is slidably movable along a needle 16 from a proximal position where a distal end 14 of the needle 16 is exposed, to a distal position where the safety shield 10 protects the distal end 14 of the needle 16. Safety shield 10 includes a binding member 18 having an aperture 22 through which the needle 16 passes. The binding member 18 also has binding surfaces 22 for binding to a medical needle 16. The safety shield 10 also includes a retainer 24 integral with the binding member 18 and in communication with the needle 16 for temporarily retaining the binding surfaces 22 in a non-binding position relative to the needle 16. The positioning member 26 illustrated in FIGS. 1-7 comprises a leaf spring integral to the binding member 18. The safety shield 10 also includes a positioning member 26 for positioning the binding surfaces 22 in a binding orientation to secure the safety shield 10 to the needle 16 when a portion 36 of the retainer 24 in contact with the needle 16 is advanced past the distal end 14 of the needle 16 and allows the retainer 24 to release from the needle 16 and move out of an axial path defined by the needle 16. The retainer 24 may also be configured such that it does not move out of an axial path defined by the needle 16. The housing 12 may further include needle supports 38 for guiding the needle through the safety shield 10. A first blocking member 40 and second blocking member 42 urge the binding member 18 into a binding orientation. The first and second blocking members 40 and 42 may also be utilized to retain the binding member 18 to the housing 12. It is contemplated that housing 12 may also include features for retaining the binding member 18 to the housing 12. The binding member 18 makes contact with the housing 12 at first blocking member 40 and second blocking member 42. First blocking member 40 and second blocking member 42 are placed on opposite sides of, and at distances perpendicular to, the long axis of needle 16.

The binding member 18 is generally a stiff plate. The aperture 20 may be round, rectangular, or of any shape having binding surfaces 22 on opposing sides of the aperture 20. The aperture 20 need not be closed on all sides, such as for example "U" shaped wherein the aperture 20 may be open to one or more edges of the binding member 18. The aperture 20 is sized to allow the needle 16 to slide within the aperture 20 when the binding member 18 is positioned at one angle relative to the long axis of the needle 16 (generally close to perpendicular), and also sized so as to bring the binding surfaces 22 of the aperture 20 into binding contact with the needle 16 when the binding member 18 is positioned at a different angle relative to the long axis of the needle 16. This angle is referred to as the binding orientation.

Figure 6:
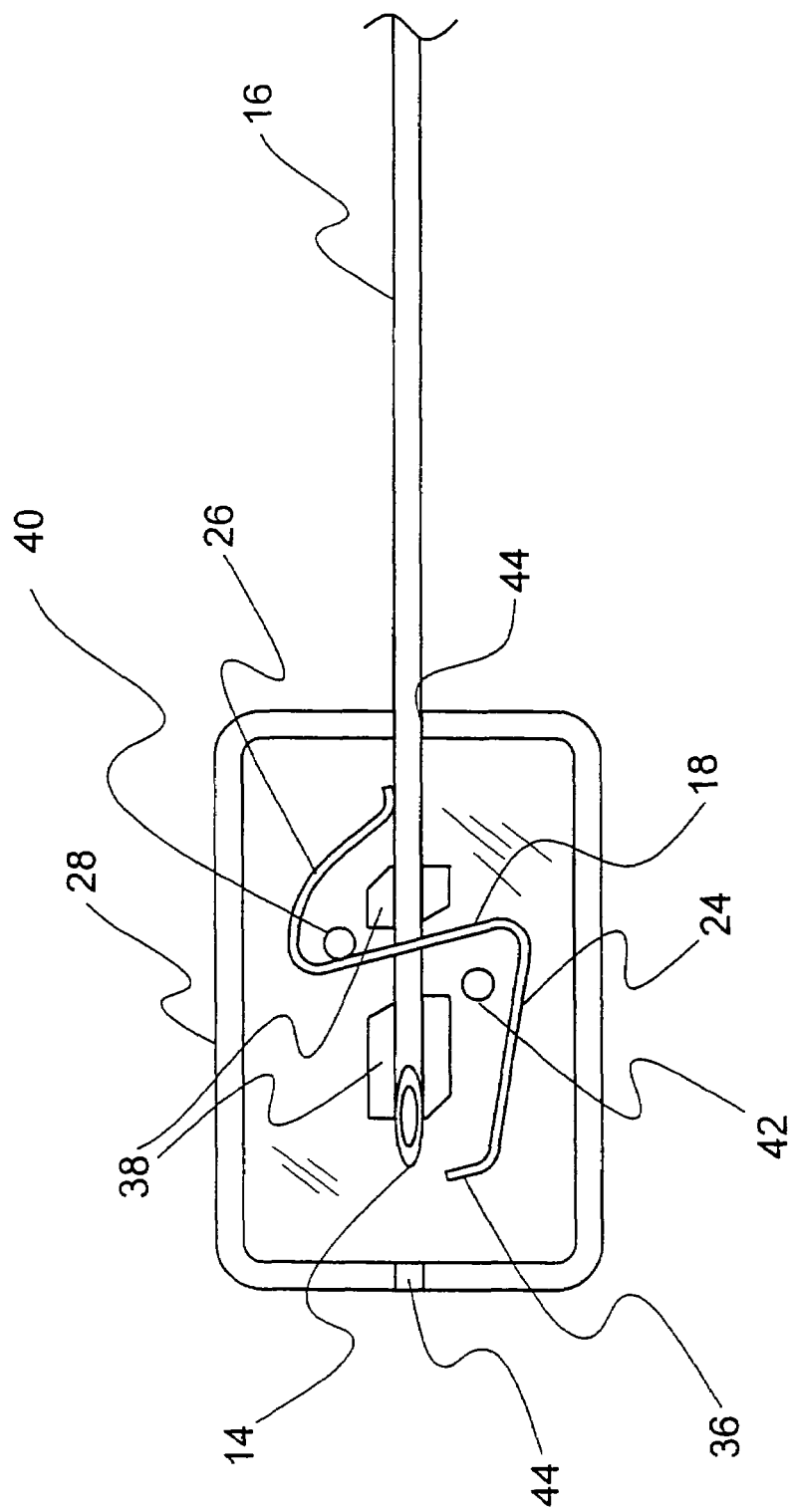
FIG. 6 is a side view of the safety shield apparatus shown in FIG. 5 with the top portion of the housing removed and showing a first blocking member of the housing urging the binding member into a binding orientation as it moves to toward the proximal end of the needle.
Figure 7:
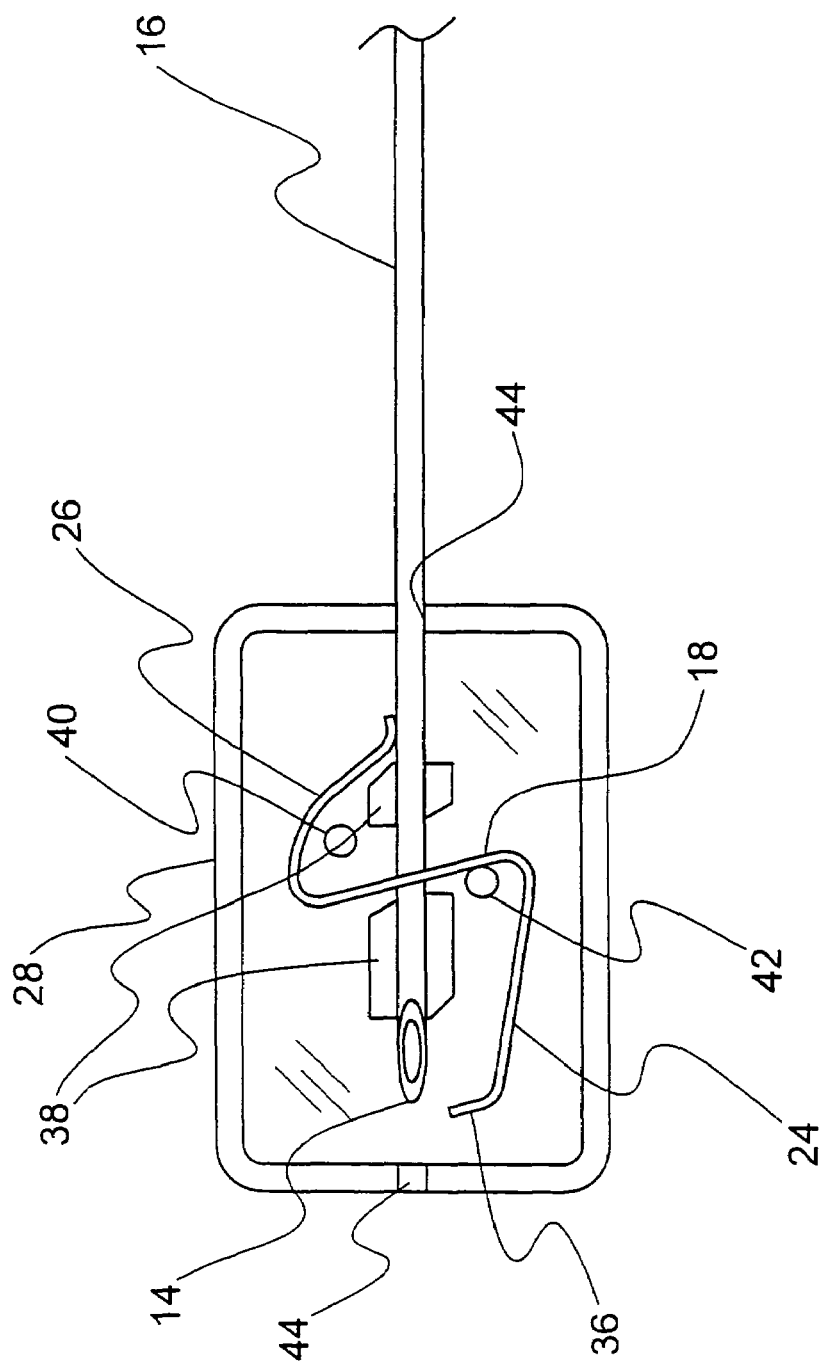
FIG. 7 is a side view of the safety shield apparatus shown in FIG. 5 with the top portion of the housing removed and showing a second blocking member of the housing urging the binding member into a binding orientation as it moves to toward the distal end of the needle.

As the safety shield 10 is urged in the proximal direction, first blocking member 40 urges the binding member 18 in a direction tending toward the binding orientation (see FIG. 6). As the safety shield 10 is urged in the distal direction, second blocking member 42 urges the binding member 18 in a direction tending toward the binding orientation (see FIG. 7).

The portion 36 on the retainer 24 in communication with the needle 16 is positioned such that when it is in contact with the needle 16, the binding member 18 is in a sliding orientation relative to the needle 16. Portion 36, by virtue of its contact with needle 16, maintains the sliding orientation of the binding member 18 by opposing the force provided by the positioning member 26, which would otherwise urge the binding member 18 into the binding position. As the safety shield 10 is moved towards the distal end 14 of the needle 16 and positioned such that portion 36 is distal of the distal end 14 of the needle 16, the binding member 18 is free to move into the binding orientation as urged by the positioning member 26. In this particular embodiment, portion 36 is a portion of a circular hole, but other surfaces may be utilized to accomplish the same function.

The positioning member 26 extends from the binding member 18, and is configured such that when the binding member 18 is in the sliding orientation, the positioning member 26 is slideably in contact with, and compressed against, the needle 16 in such a way as to provide a force tending to urge the binding member 18 into the binding orientation, but selectably opposed by portion 36 as described above. The binding member 18 may be unitary with a resilient positioning member 26. The positioning member 26 may take other resilient shapes such as a coil or accordion. Other portions of the binding member 18 may be more stiff, which may be accomplished by varying the geometry such as the thickness, width, etc.

Binding of the binding member 18 to the needle 16 is a function of the friction force generated between the aperture binding surfaces 22 and the needle 16. Sharp edges are advantageous, but not required. The friction force generated is a function of the aperture 20 dimension, the needle 16 diameter, the binding member 18 thickness, the distance between the first and second blocking members 40 and 42 to the centerline of the needle 16, and the coefficient of friction between the aperture 20 and the needle 16. One skilled in the art may easily derive an equation demonstrating that these key elements may be arranged in such a way as to ensure that the friction force generated will always be sufficient to bind the binding member 18 to the needle 18 for any force applied to the safety shield 10 up to the point of material failure of at least one of the elements.

Safety shield 10 can be fabricated from a material suitable for medical applications, such as, for example, polymerics or metals, such as stainless steel, depending on the particular medical application and/or preference of a clinician. Semi-rigid and rigid polymerics are contemplated for fabrication, as well as resilient materials, such as molded medical grade polypropylene. However, one skilled in the art will realize that other materials and fabrication methods suitable for assembly and manufacture, in accordance with the present disclosure, also would be appropriate.

Figure 8:
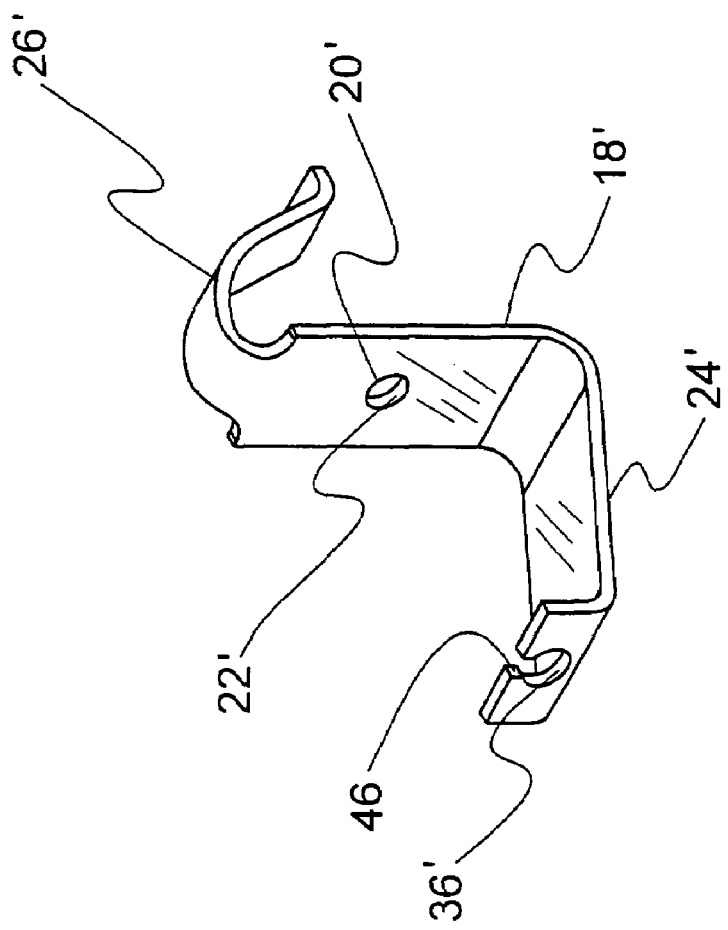
FIG. 8 is a perspective view of the safety shield apparatus illustrated in FIG. 1 showing an alternate retainer embodiment, which includes a slot for permitting a guidewire to extend through the safety shield apparatus.
Figure 9:
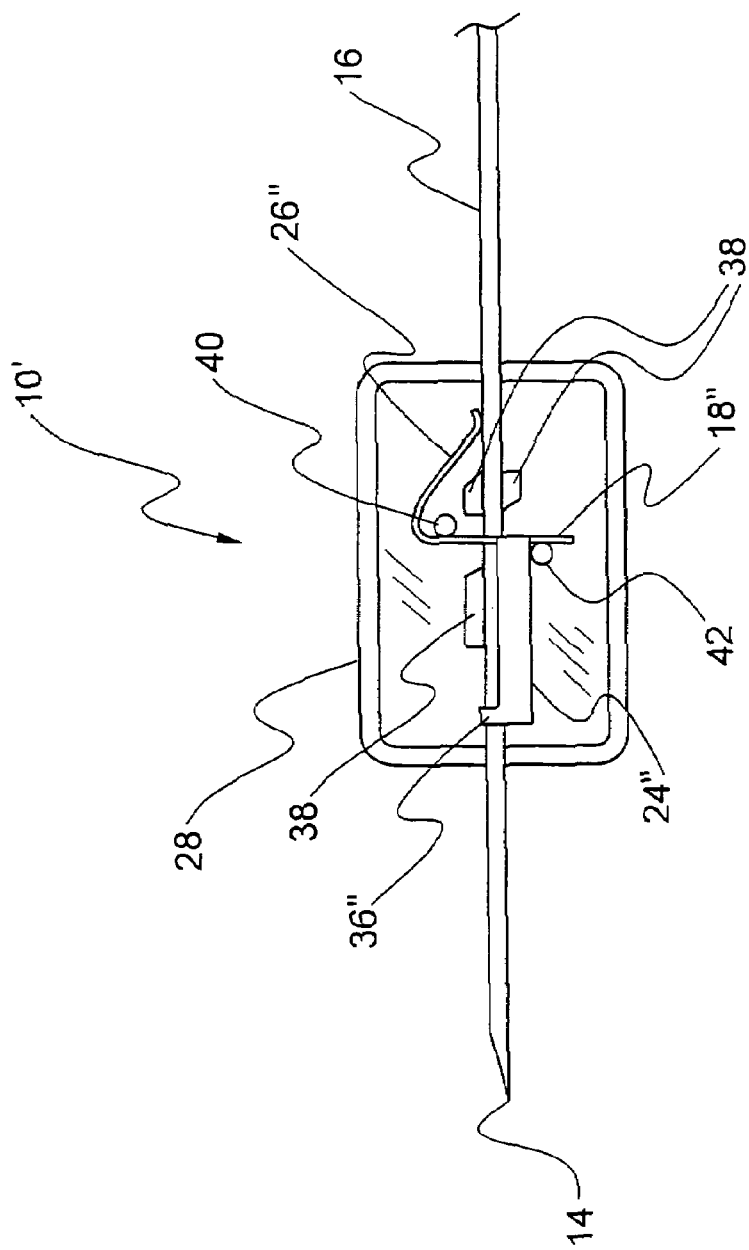
FIG. 9 is a side view of the safety shield apparatus illustrated in FIG. 1 with the top portion of the housing removed and showing an alternate binding member and retainer embodiment.

Safety shield 10 may also be adapted for use with a medical needle device having a guidewire introducer, such as a Seldinger needle. An alternate embodiment of retainer 24' is shown in FIG. 8, which includes a slot 46 for permitting a guidewire, stylet, or other element passed through the bore of needle 16, to extend through the safety shield 10. Similar to the binding member 18 shown in FIGS. 1-7, the binding member 18' includes an aperture 22' through which the needle 16 passes. The binding member 18' also has binding surfaces 22' for binding to a medical needle 16. A retainer 24' integral with the binding member 18' communicates with the needle 16 for temporarily retaining the binding surfaces 22' in a non-binding position relative to the needle 16. The positioning member 26' illustrated in FIG. 8 comprises a leaf spring integral to the binding member 18'. Positioning member 26' positions the binding surfaces 22' to secure the safety shield 10' to the needle 16 when a portion 36' of the retainer 24' in contact with the needle 16 is advanced past the distal end 14 of the needle 16 and allows the retainer 24' to release from the needle 16 and move out of an axial path defined by the needle 16.

Figure 10:
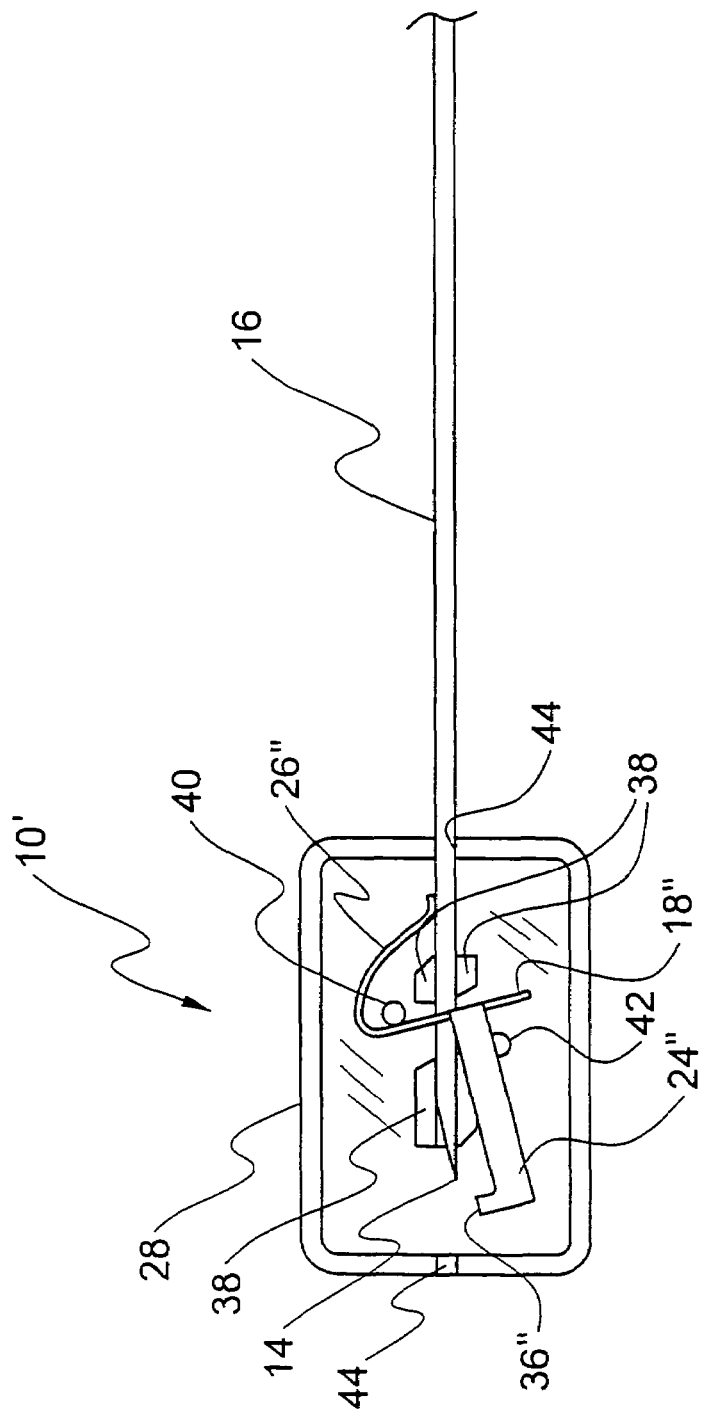
FIG. 10 is a side view of the safety shield apparatus shown in FIG. 5 with the top portion of the housing removed and showing a first blocking member of the housing urging the binding member into a binding orientation as it moves to toward the proximal end of the needle.
Figure 11:
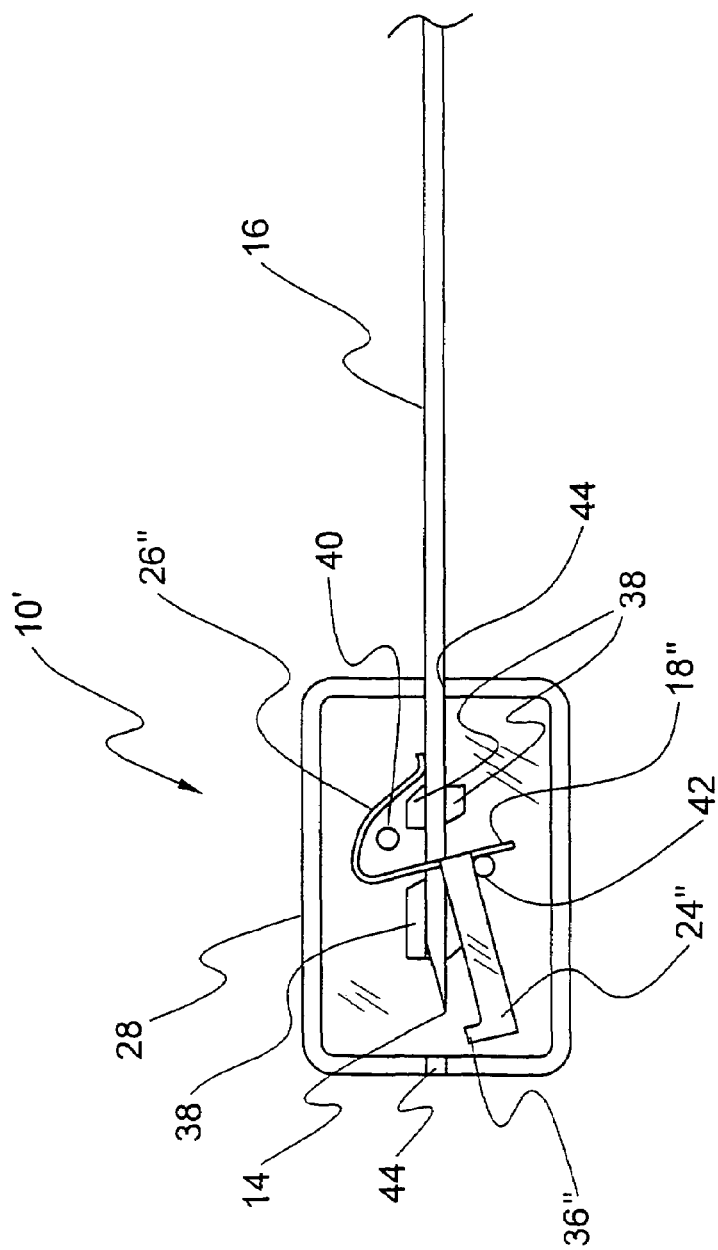
FIG. 11 is a side view of the safety shield apparatus shown in FIG. 5 with the top portion of the housing removed and showing a second blocking member of the housing urging the binding member into a binding orientation as it moves to toward the distal end of the needle.
Figure 12:
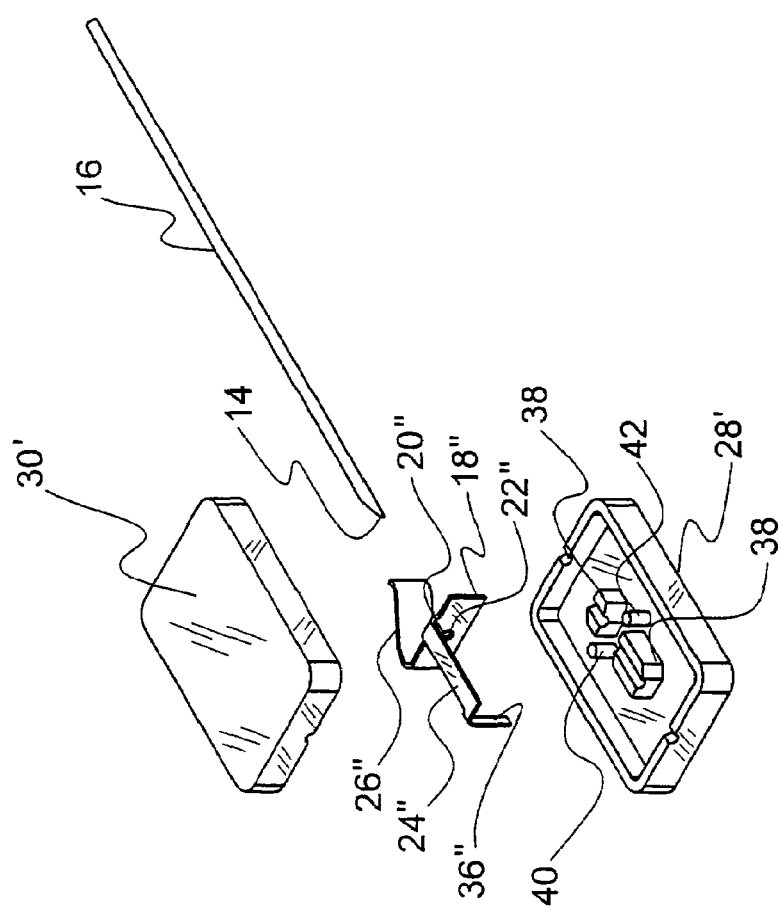
FIG. 12 is a perspective view of the safety shield apparatus illustrated in FIG. 9 with the components separated.
Figure 13:
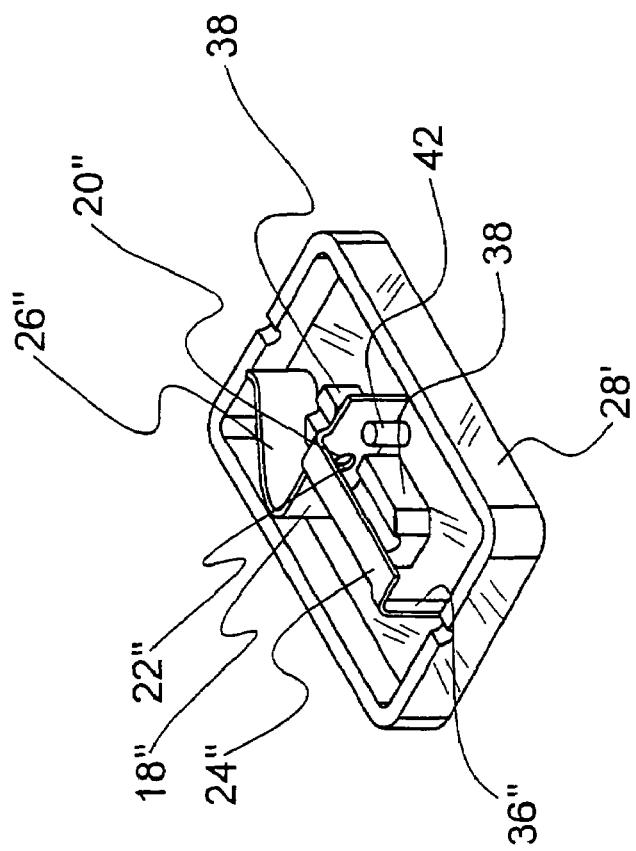
FIG. 13 is a perspective view of a portion of the components of the safety shield apparatus shown in FIG. 9.
Figure 14:
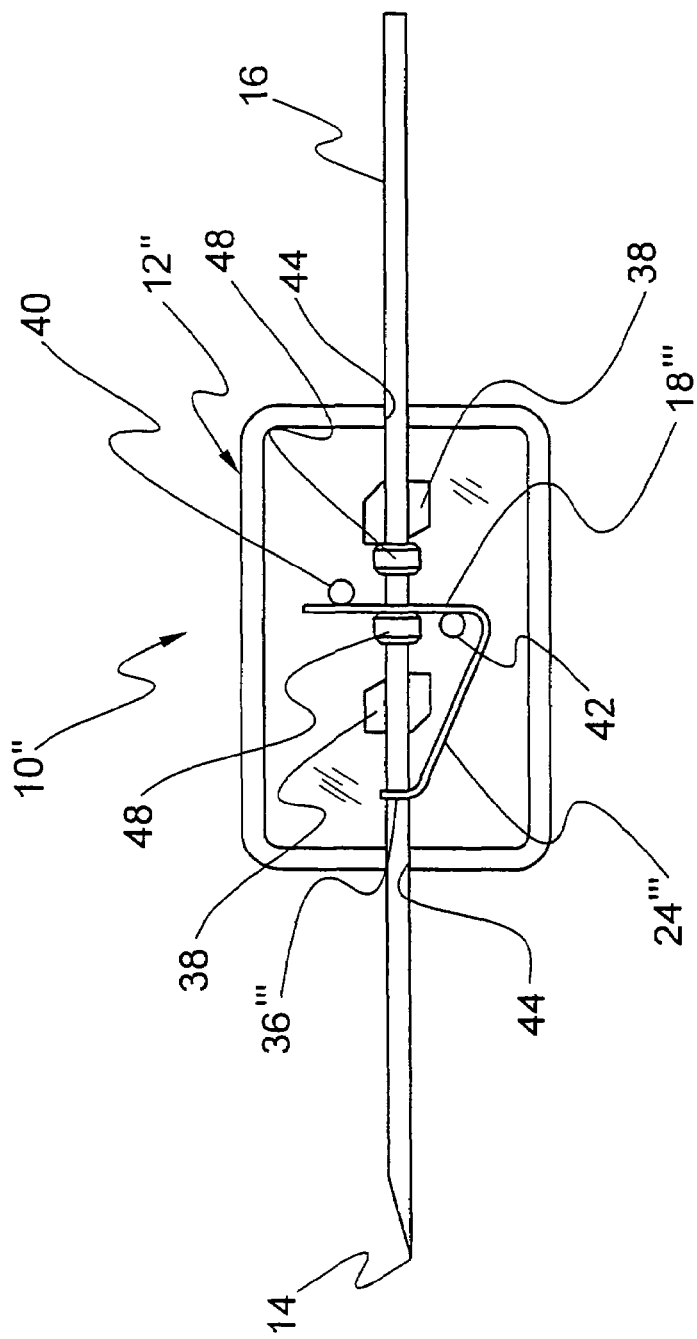
FIG. 14 is a side view of the safety shield apparatus illustrated in FIG. 1 with the top portion of the housing removed and showing an alternate binding member and positioning member embodiment.

An alternate embodiment of retainer 24" is illustrated in FIGS. 9-13, wherein the portion 36" on retainer 24" in communication with needle 16 comprises a planar surface in contact with the needle 16. Safety shield 10' is slidably movable along a needle 16 from a proximal position where a distal end 14 of the needle 16 is exposed, to a distal position where the safety shield 10' protects the distal end 14 of the needle 16. Safety shield 10' includes a binding member 18" having an aperture 22" through which the needle 16 passes. The binding member 18" also has binding surfaces 22" for binding to a medical needle 16. The safety shield 10' also includes a retainer 24" integral with the binding member 18" and in communication with the needle 16 for temporarily retaining the binding surfaces 22" in a non-binding position relative to the needle 16. The positioning member 26" illustrated in FIGS. 9-13 comprises a leaf spring integral to the binding member 18". The safety shield 10' also includes a positioning member 26" for positioning the binding surfaces 22" to secure the safety shield 10' to the needle 16 when a portion 36" of the retainer 24" in contact with the needle 16 is advanced past the distal end 14 of the needle 16 and allows the retainer 24" to release from the needle 16 and move out of an axial path defined by the needle 16. The housing 12 may further include needle supports 38 for guiding the needle 16 through the safety shield 10'. A first blocking member 40 and second blocking member 42 may be provided to urge the binding member 18" into a binding orientation. First blocking member 40 urges the binding member 18" into a binding orientation as it is moved towards the proximal end of needle 16, as shown in FIG. 10. Second blocking member 42 urges the binding member 18" into a binding orientation as it is moved towards the distal end 14 of needle 16, as shown in FIG. 11.

Figure 15:
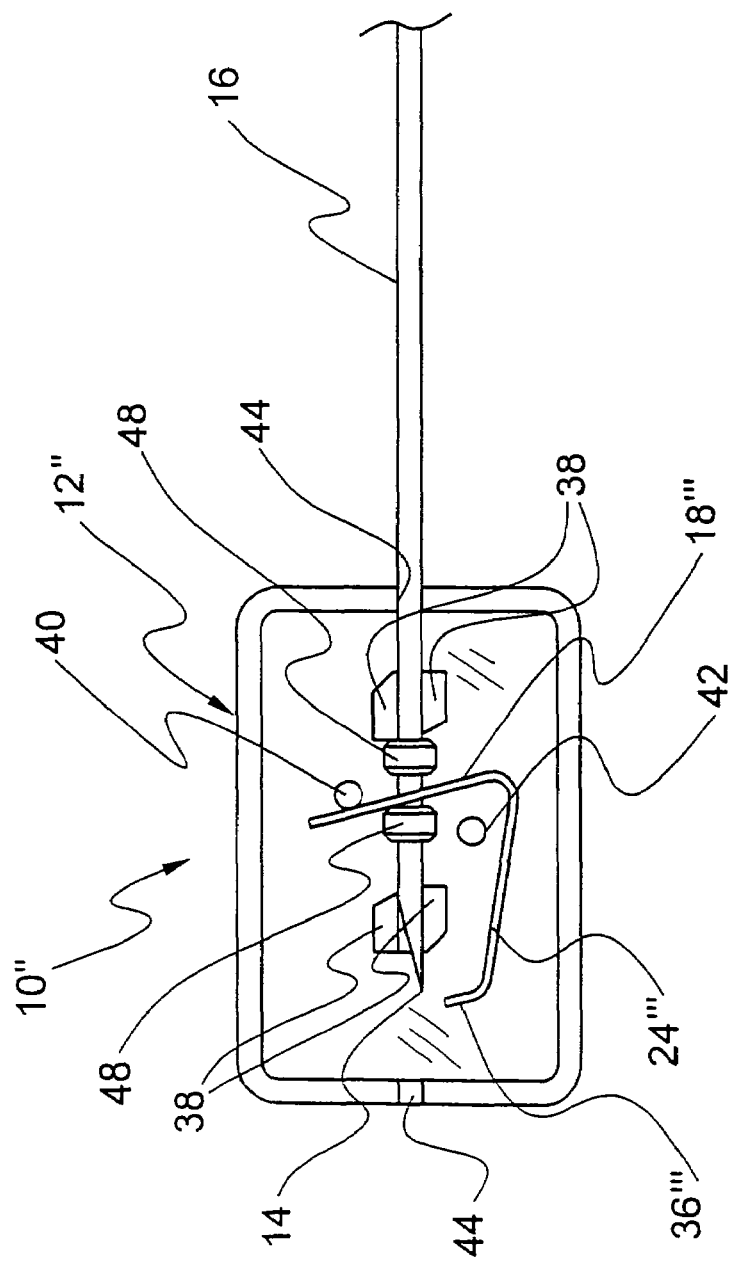
FIG. 15 is a side view of the safety shield apparatus shown in FIG. 14 with the top portion of the housing removed and showing a first blocking member of the housing urging the binding member into a binding orientation as it moves to toward the proximal end of the needle.
Figure 16:
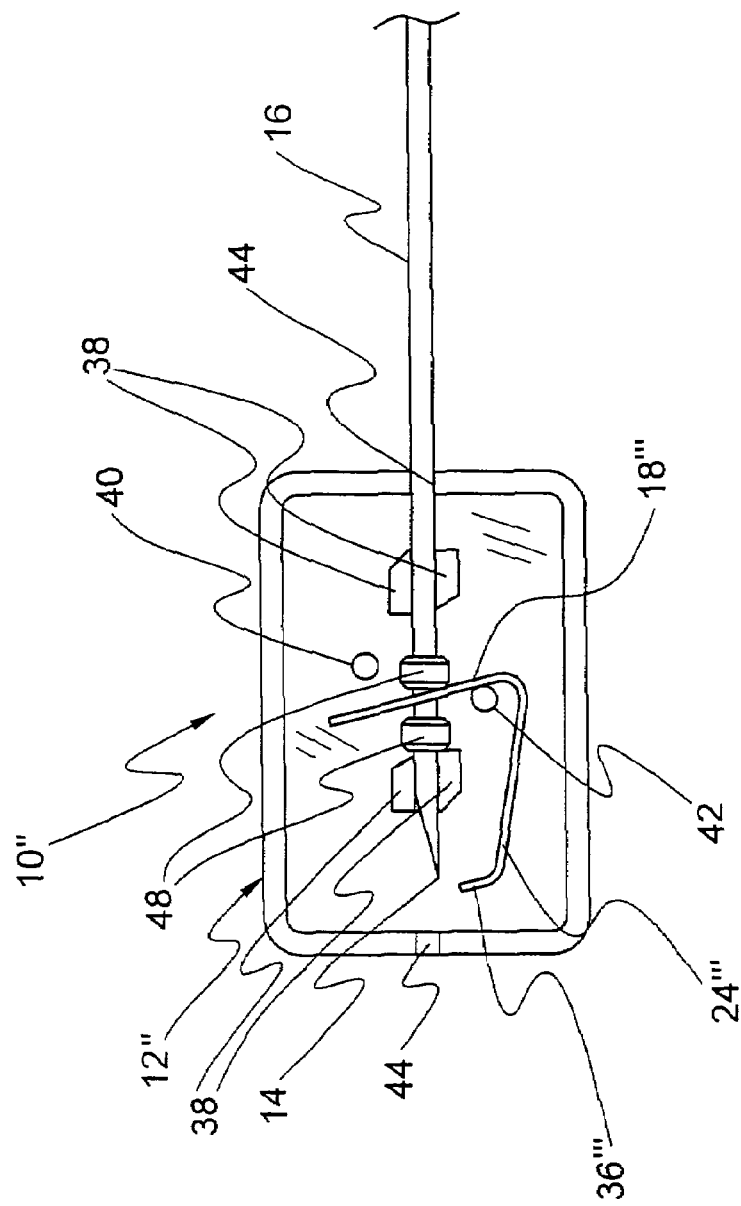
FIG. 16 is a side view of the safety shield apparatus shown in FIG. 14 with the top portion of the housing removed and showing a second blocking member of the housing urging the binding member into a binding orientation as it moves to toward the distal end of the needle.
Figure 17:
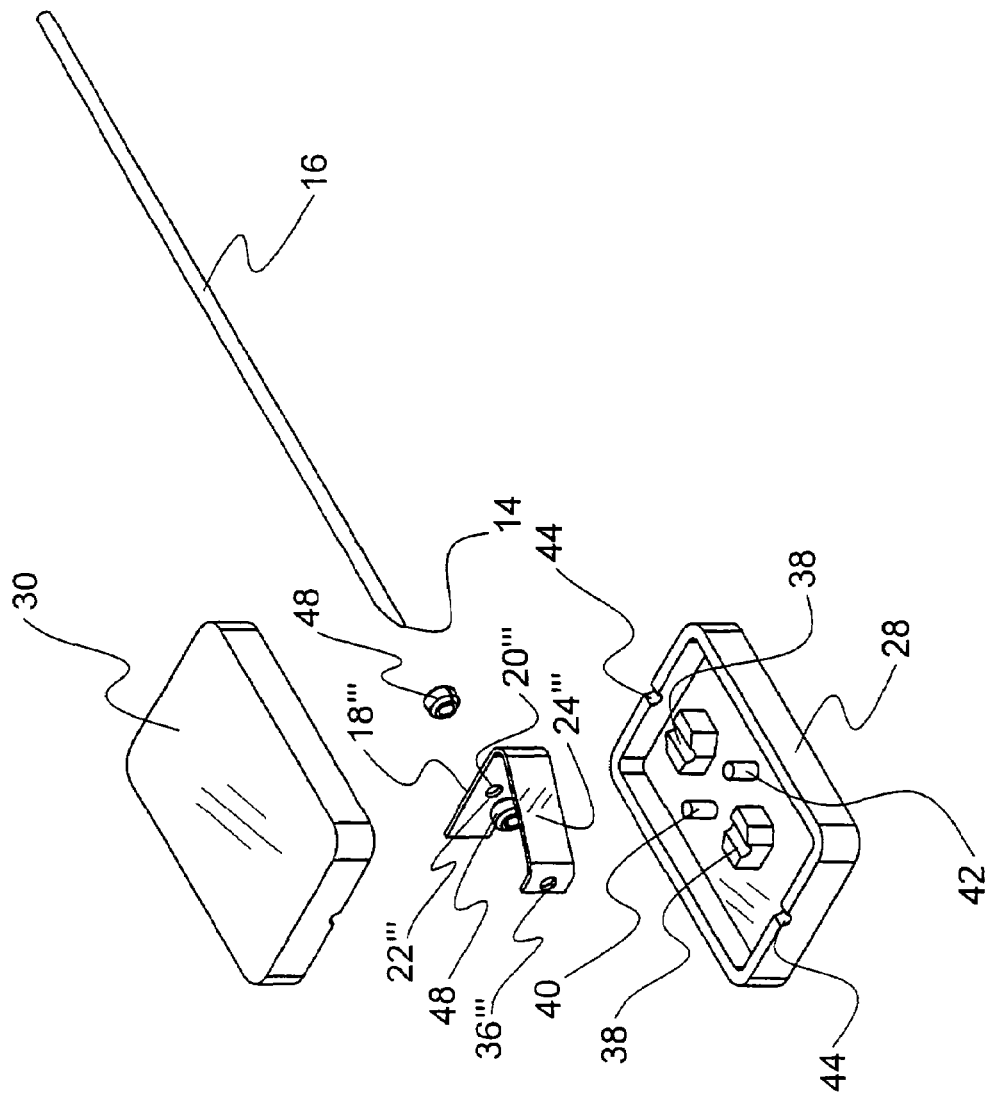
FIG. 17 is a perspective view of the safety shield apparatus illustrated in FIG. 14 with the components separated.
Figure 18:
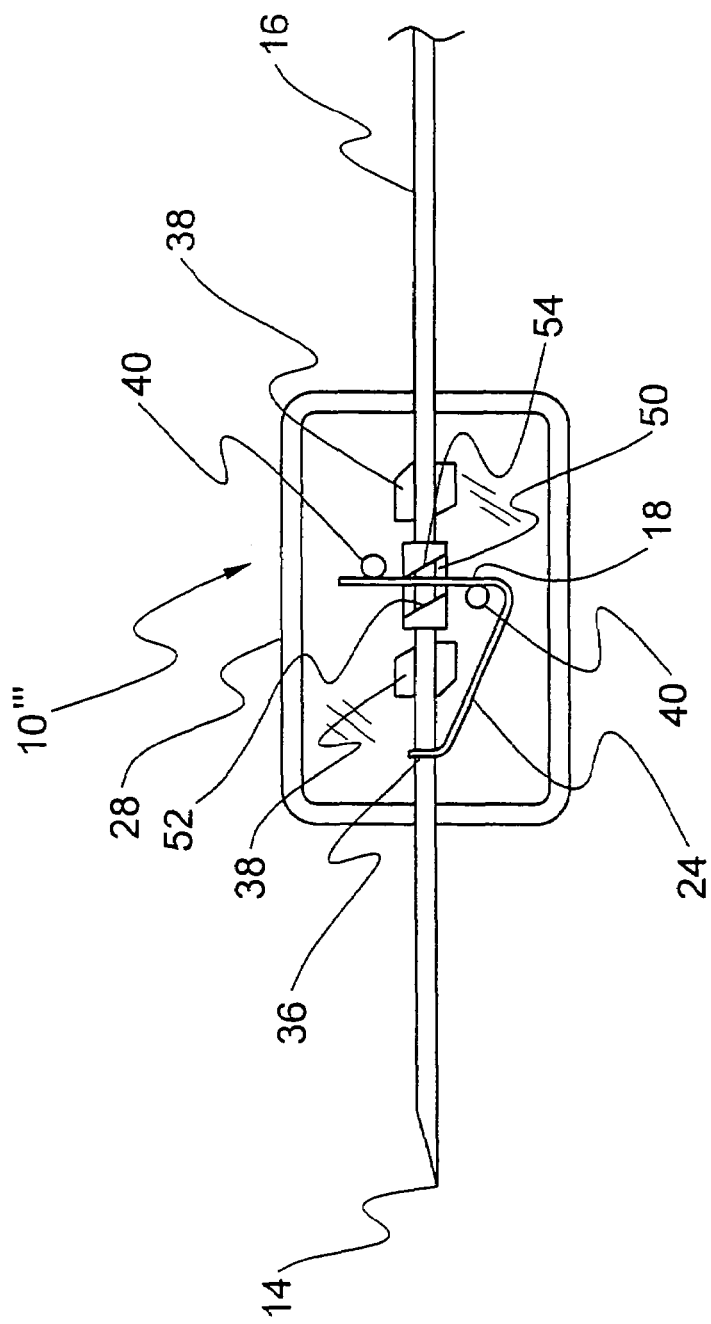
FIG. 18 is a side view of the safety shield apparatus illustrated in FIG. 1 showing an alternate binding member and positioning member embodiment.

An alternate embodiment of positioning member is illustrated in FIGS. 14-17, wherein the positioning member comprises friction elements 48 having a sliding friction fit on the needle 16. Safety shield 10" is slidably movable along a needle 16 from a proximal position where a distal end 14 of the needle 16 is exposed, to a distal position where the safety shield 10" protects the distal end 14 of the needle 16. Safety shield 10" includes a binding member 18'" having an aperture 22'" through which the needle 16 passes. The binding member 18'" also has binding surfaces 22'" for binding to a medical needle 16. The safety shield 10" also includes a retainer 24'" integral with the binding member 18'" and in communication with the needle 16 for temporarily retaining the binding surfaces 22'" in a non-binding position relative to the needle 16. The combination of the force generated by the friction elements 48, the force input from the first blocking member 40 or second blocking member 42 upon interface with binding member 18'", and the lever or moment arm formed by the binding member 18'" forms a couple which provides a force tending to urge the binding member 18'" into binding orientation. The friction elements 48 thus position the binding surfaces 22'" to secure the safety shield 10" to the needle 16 when a portion 36'" of the retainer 24'" in contact with the needle 16 is advanced past the distal end of the needle 16 and allows the retainer 24'" to release from the needle 16. The housing 12 may further include needle supports 38 for guiding the needle 16 through the safety shield 10". A first blocking member 40 and second blocking member 42 may be provided to urge the binding member 18'" into binding orientation. First blocking member 40 urges binding member 18'" into a binding orientation as it is moved towards the proximal end of needle 16, as shown in FIG. 15. Second blocking member 42 urges binding member 18'" into a binding orientation as it is moved towards the distal end 14 of needle 16, as shown in FIG. 16.

Figure 19:
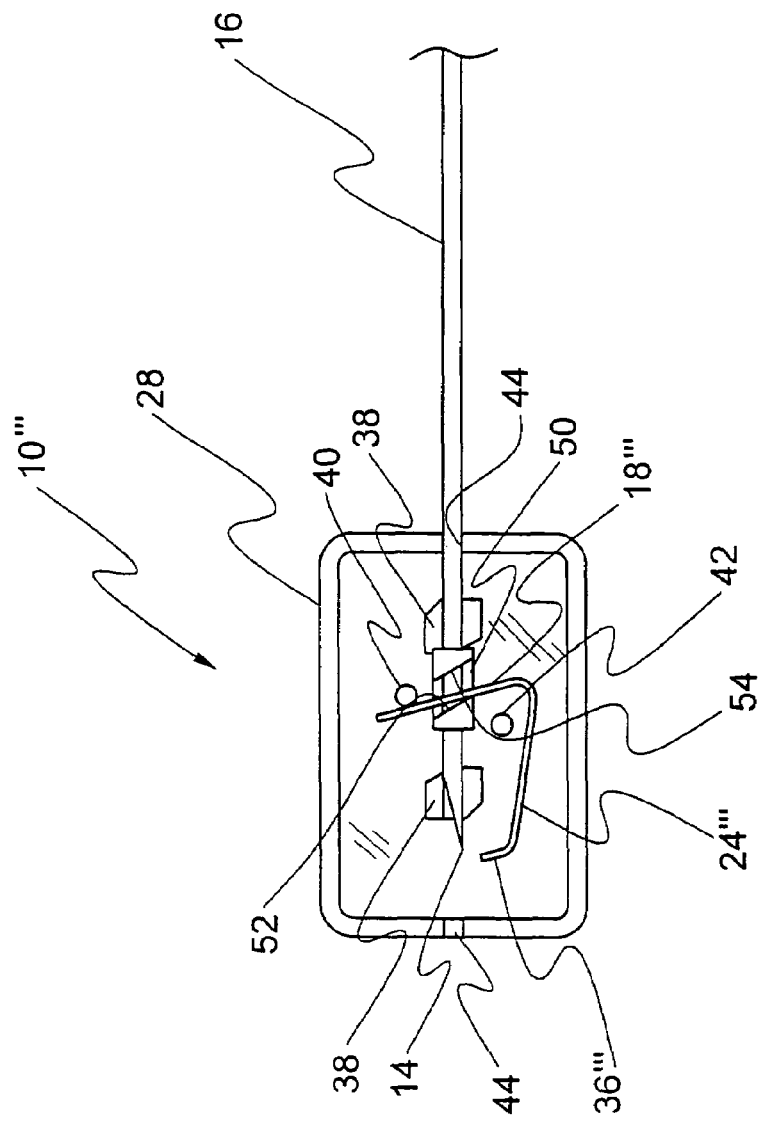
FIG. 19 is a side view of the safety shield apparatus shown in FIG. 18 with the top portion of the housing removed and showing a first blocking member of the housing urging the binding member into a binding orientation as it moves to toward the proximal end of the needle.
Figure 20:
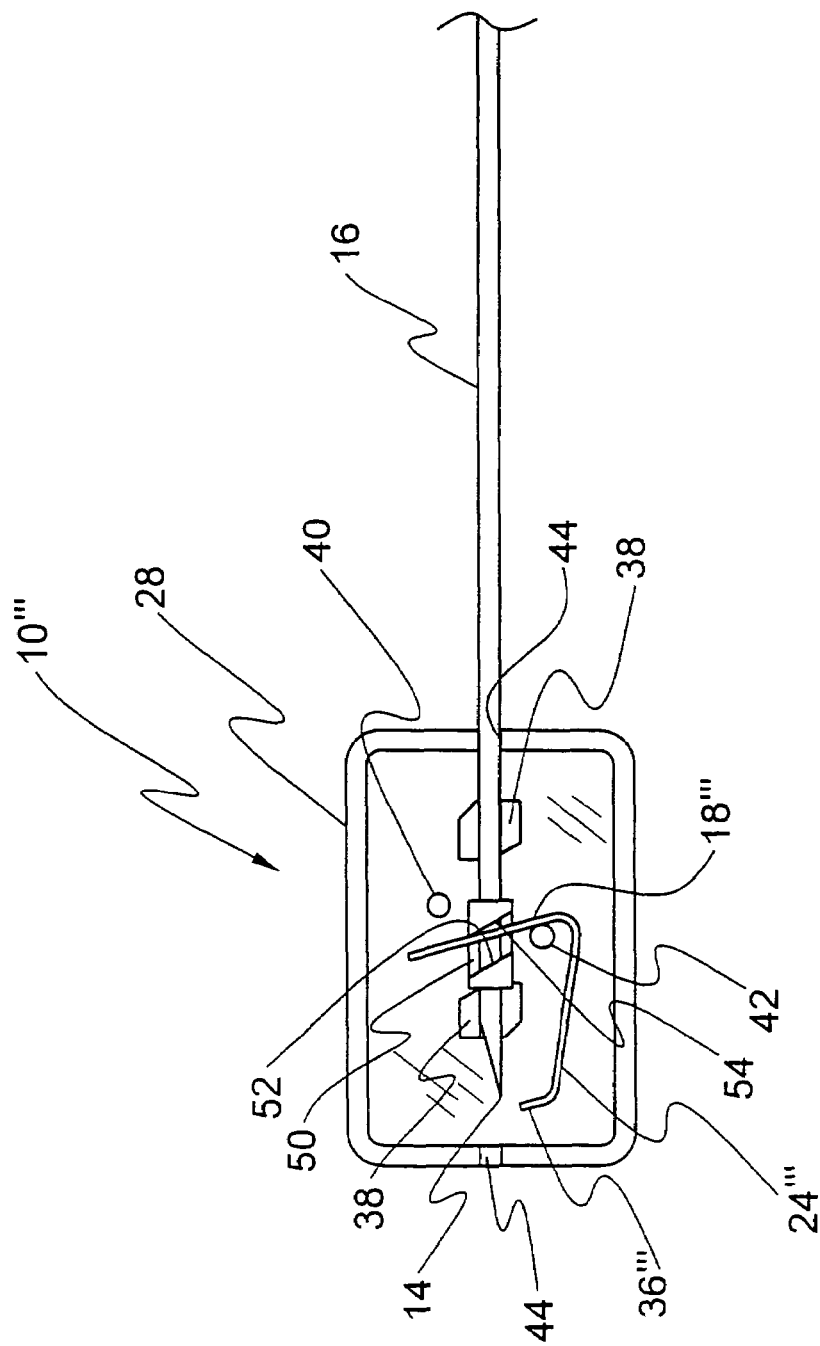
FIG. 20 is a side view of the safety shield apparatus shown in FIG. 18 with the top portion of the housing removed and showing a second blocking member of the housing urging the binding member into a binding orientation as it moves to toward the distal end of the needle.
Figure 21A:
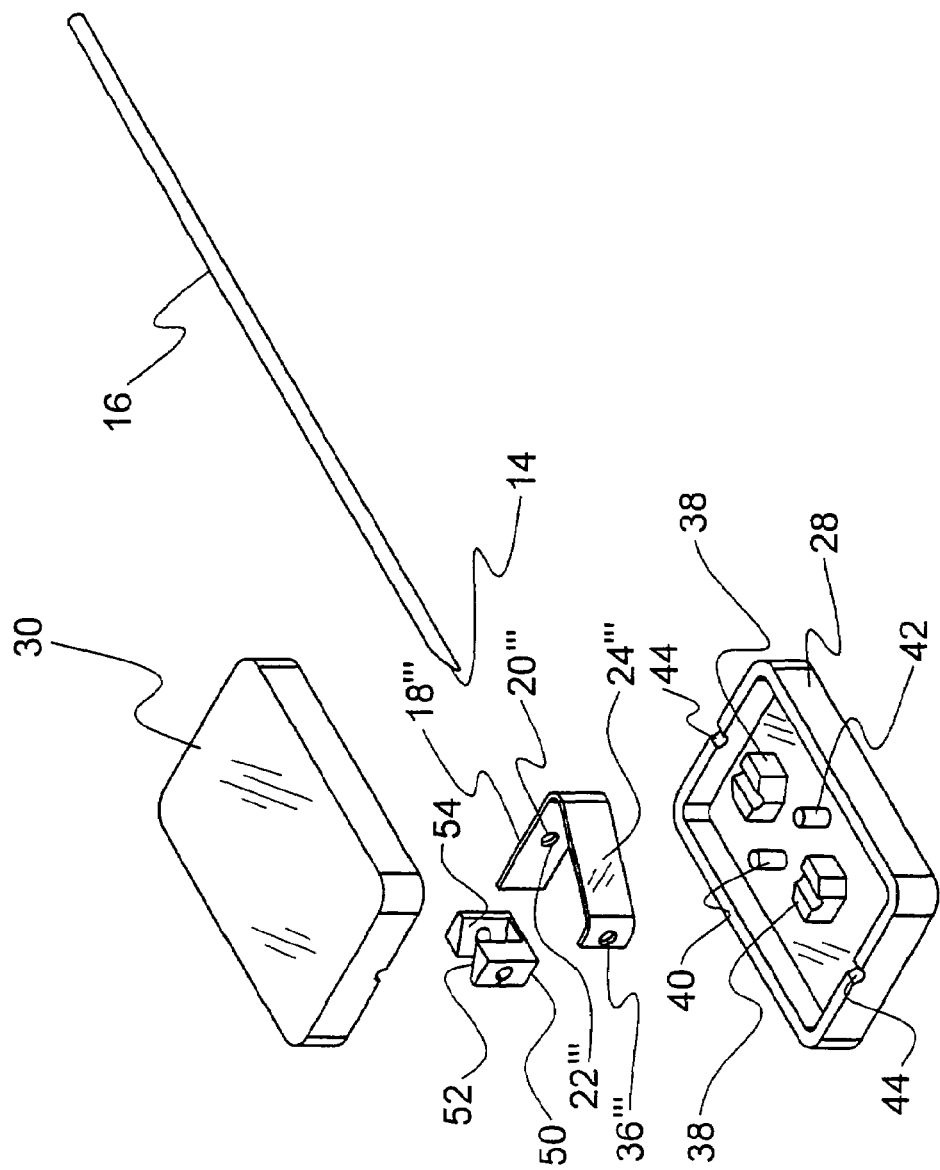
FIG. 21A is a perspective view of the safety shield apparatus illustrated in FIG. 18 with the components separated.
Figure 21B:
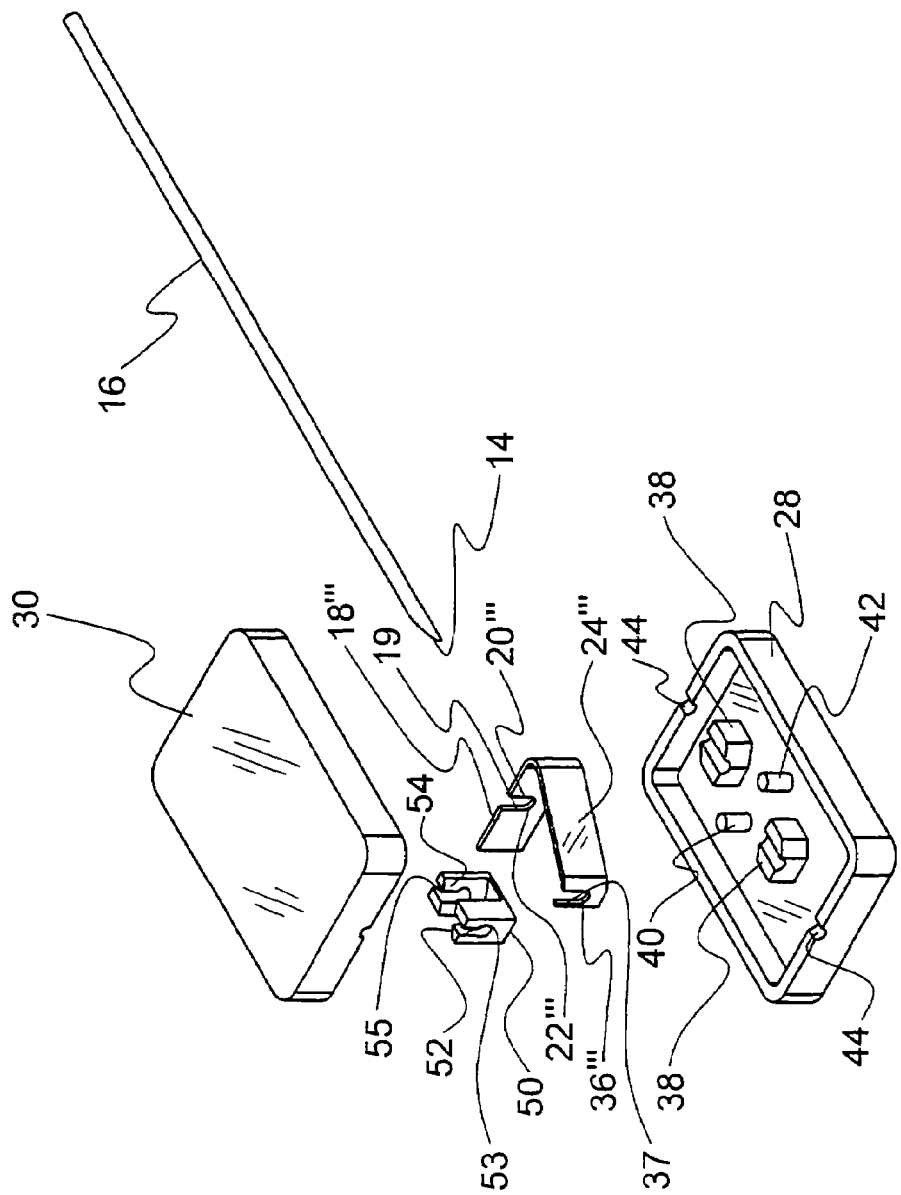
FIG. 21B is a perspective view of the safety shield apparatus illustrated in FIG. 18 with the components separated and showing an alternate binding member embodiment.

The friction elements 48, as described above, may be joined to create a unitary friction element 50 as shown in FIGS. 18-21. Safety shield 10'" is slidably movable along a needle 16 from a proximal position where a distal end 14 of the needle 16 is exposed, to a distal position where the safety shield 10'" protects the distal end 14 of the needle 16. Safety shield 10'" includes a binding member 18'" having an aperture 22'" through which the needle 16 passes. The binding member 18'" also has binding surfaces 22'" for binding to a medical needle 16. The safety shield 10'" also includes a retainer 24'" integral with the binding member 18'" and in communication with the needle 16 for temporarily retaining the binding surfaces 22'" in a non-binding position relative to the needle 16. The combination of the force generated by the first surface 52 and second surface 54 of unitary friction elements 50, the force input from the first blocking member 40 or second blocking member 42 upon interface with binding member 18'", and the lever or moment arm formed by the binding member 18'" forms a couple which provides a force tending to urge the binding member 18'" into binding orientation. It is also contemplated that other geometries may be utilized which accomplish the same function as first surface 52 and second surface 54. The unitary friction element 50 thus positions the binding surfaces 22'" to secure the safety shield 10'" to the needle 16 when a portion 36'" of the retainer 24'" in contact with the needle 16 is advanced past the distal end 14 of the needle 16 and allows the retainer 24'" to release from the needle 16. The housing 12 may further include needle supports 38 for guiding the needle 16 through the safety shield 10'". A first blocking member 40 and second blocking member 42 may be provided to urge the binding member 18'" into binding orientation. First blocking member 40 urges the binding member 18'" into a binding orientation as it is moved towards the proximal end of needle 16, as shown in FIG. 19. Second blocking member 42 urges the binding member 18'" into a binding orientation as it is moved towards the distal end 14 of needle 16, as shown in FIG. 20.

The binding member 18'" and portion 36'" on retainer 24'" may include "U" shaped apertures 19 and 37 respectively, as well as "U" shaped openings 53 and 55 on first surface 52 and second surface 54 respectively, to provide side installation of the needle 16 during assembly of the safety shield 10'".

Figure 22:
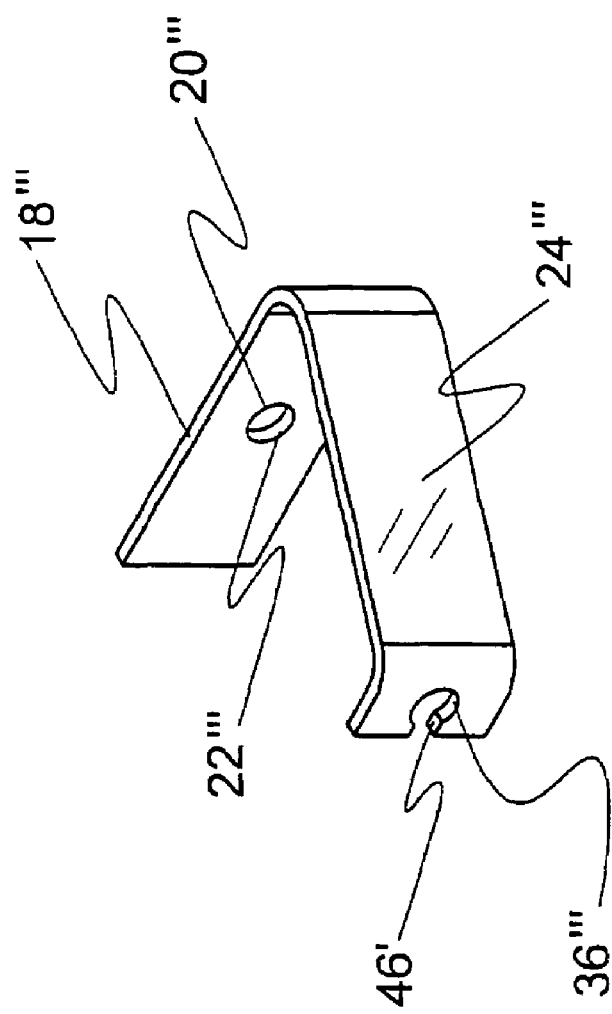
FIG. 22 is a perspective view of the safety shield apparatus illustrated in FIGS. 14 and 18 showing an alternate retainer embodiment, which includes a slot for permitting a guidewire to extend through the safety shield apparatus.
Figure 23:
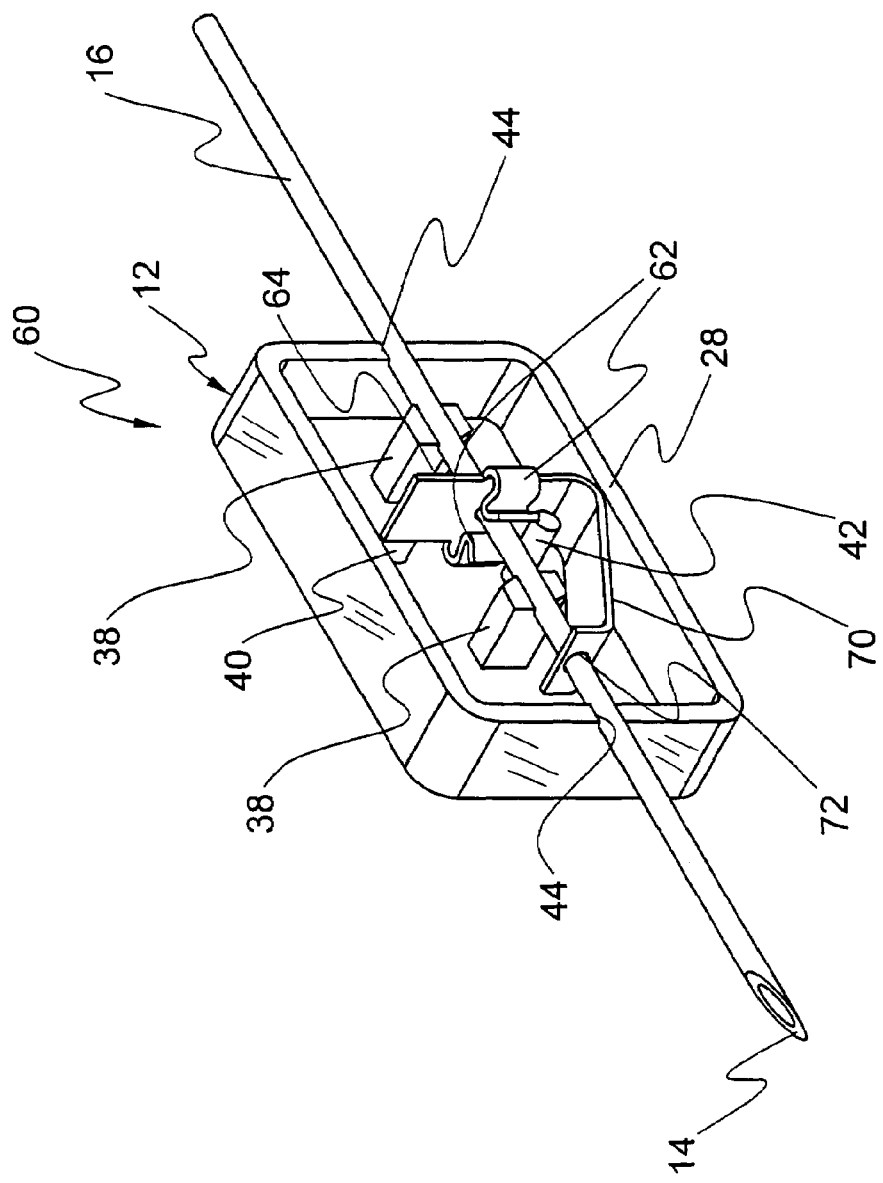
FIG. 23 is a perspective view of the safety shield apparatus illustrated in FIG. 1 with the top portion of the housing removed and showing an alternate binding member and positioning member embodiment.

Safety shields 10" and 10'" may also be adapted for use with a medical needle device having a guidewire introducer, such as a Seldinger needle. An alternate embodiment of retainer 24'" is shown in FIG. 22, which includes a slot 46' for permitting a guidewire to extend through the safety shield 10" or 10'". Similar to the binding members 18" and 18'" shown in FIGS. 14-21, the binding member 18'" includes an aperture 22'" through which the needle 16 passes. The binding member 18'" also has binding surfaces 22'" for binding to a medical needle 16. A retainer 24'" integral with the binding member

18''' communicates with the needle 16 for temporarily retaining the binding surfaces 22''' in a non-binding position relative to the needle 16.

Figure 24:
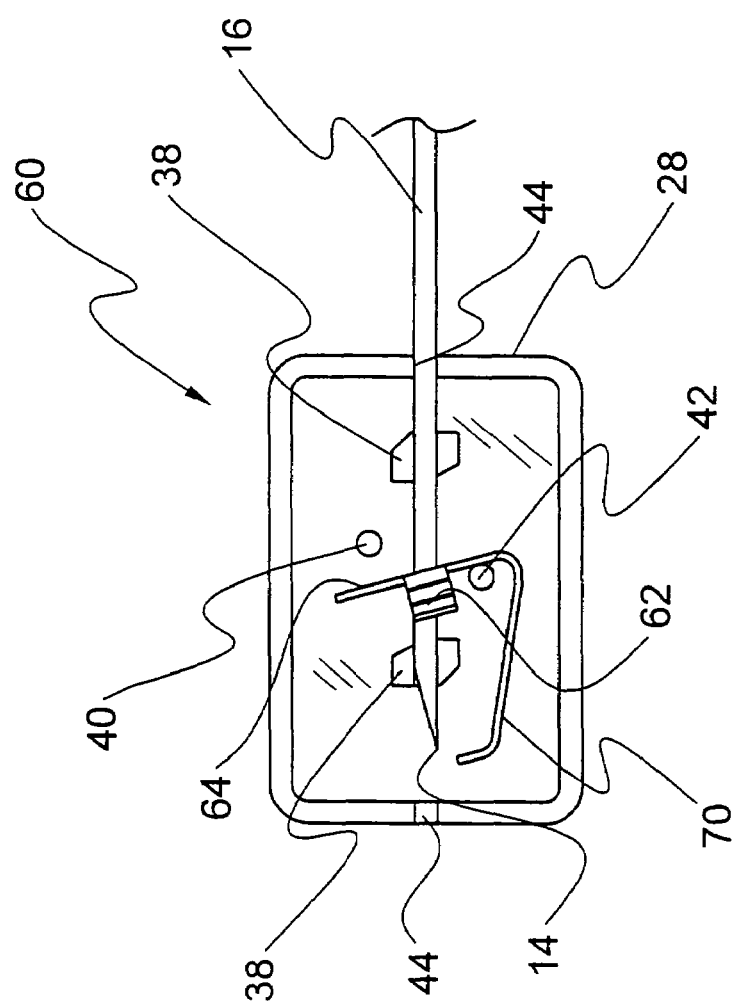
FIG. 24 is a side view of the safety shield apparatus shown in FIG. 23 with the top portion of the housing removed and showing a first blocking member of the housing urging the binding member into a binding orientation as it moves to toward the proximal end of the needle.
Figure 25:
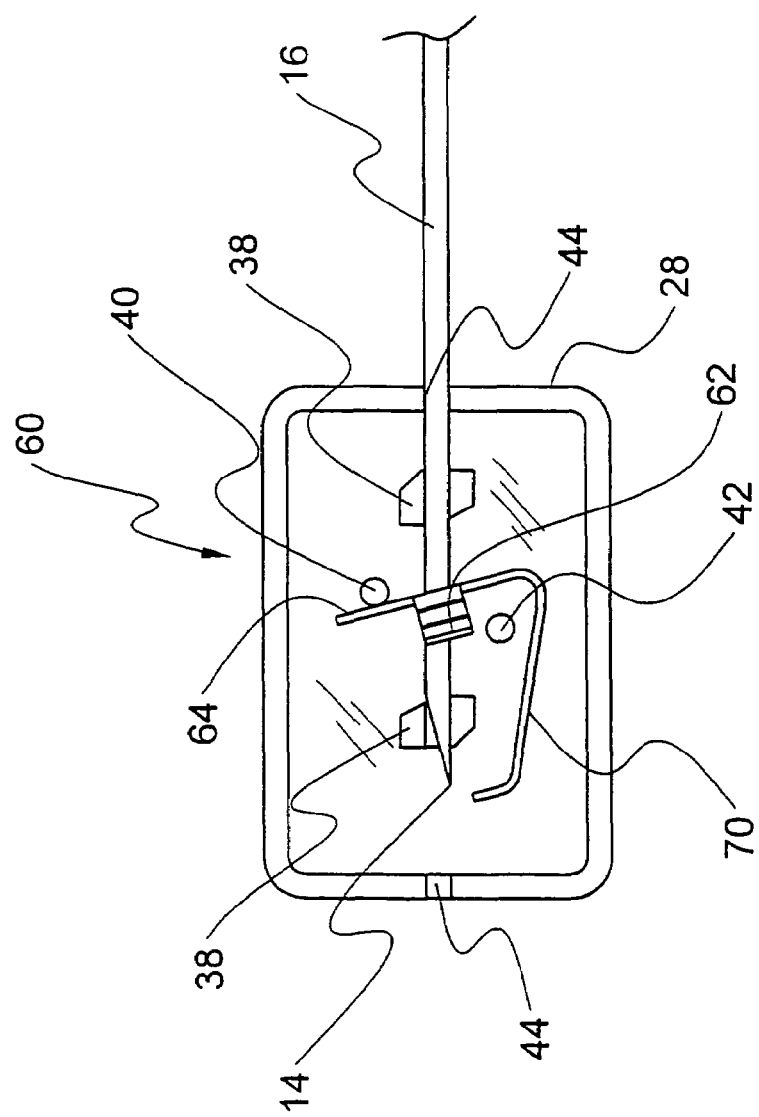
FIG. 25 is a side view of the safety shield apparatus shown in FIG. 23 with the top portion of the housing removed and showing a second blocking member of the housing urging the binding member into a binding orientation as it moves to toward the distal end of the needle.
Figure 26:
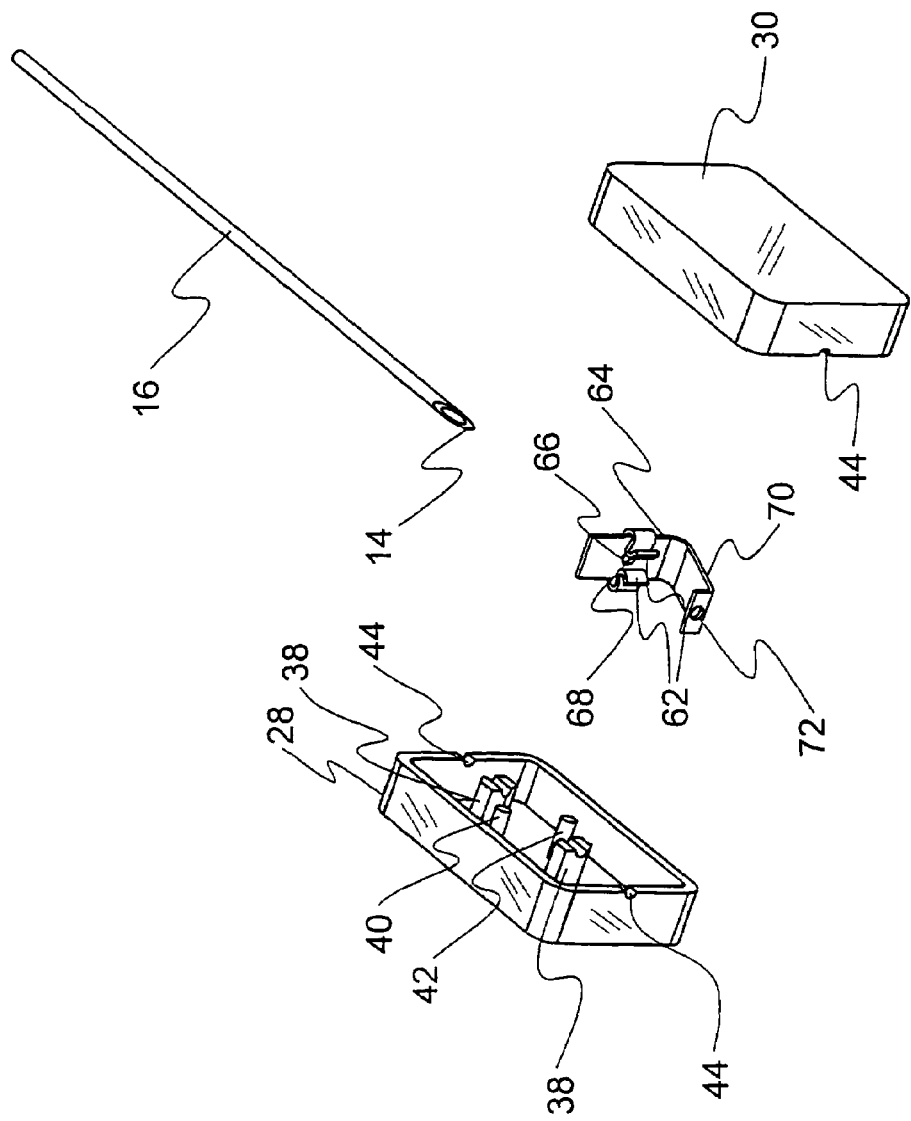
FIG. 26 is a perspective view of the safety shield apparatus illustrated in FIG. 23 with the components separated.

The friction elements 62 may also be integral to the binding member 64 as shown in FIGS. 23-27. Other friction element 62 configurations are contemplated which accomplish the same function of creating drag on the needle in such a way as to selectably promote binding. Safety shield 60 is slidably movable along a needle 16 from a proximal position where a distal end 14 of the needle 16 is exposed, to a distal position where the safety shield 60 protects the distal end 14 of the needle 16. Safety shield 60 includes a binding member 64 having an aperture 66 through which the needle 16 passes. The binding member 64 also has binding surfaces 68 for binding to a medical needle 16. The safety shield 60 also includes a retainer 70 integral with the binding member 64 and in communication with the needle 16 for temporarily retaining the binding surfaces 68 in a non-binding position relative to the needle 16. The combination of the force generated by the friction elements 62, the force input from the first blocking member 40 or second blocking member 42 upon interface with binding member 64, and the lever or moment arm formed by the binding member 64 forms a couple which provides a force tending to urge the binding member 64 into a binding orientation. The friction elements 62 thus position the binding surfaces 68 to secure the safety shield 60 to the needle 16 when a portion 72 of the retainer 70 in contact with the needle 16 is advanced past the distal end 14 of the needle 16 and allows the retainer 70 to release from the needle 16. The housing 12 may further include needle supports 38 for guiding the needle 16 through the safety shield 60. A first blocking member 40 and second blocking member 42 may be provided to urge the binding member 64 into a binding orientation. First blocking member 40 urges the binding member 64 into a binding orientation as it is moved towards the proximal end of needle 16, as shown in FIG. 24. Second blocking member 42 urges the binding member 64 into a binding orientation and retains housing 12 to the safety shield 60 as it is moved towards the distal end 14 of needle 16, as shown in FIG. 25.

Figure 27:
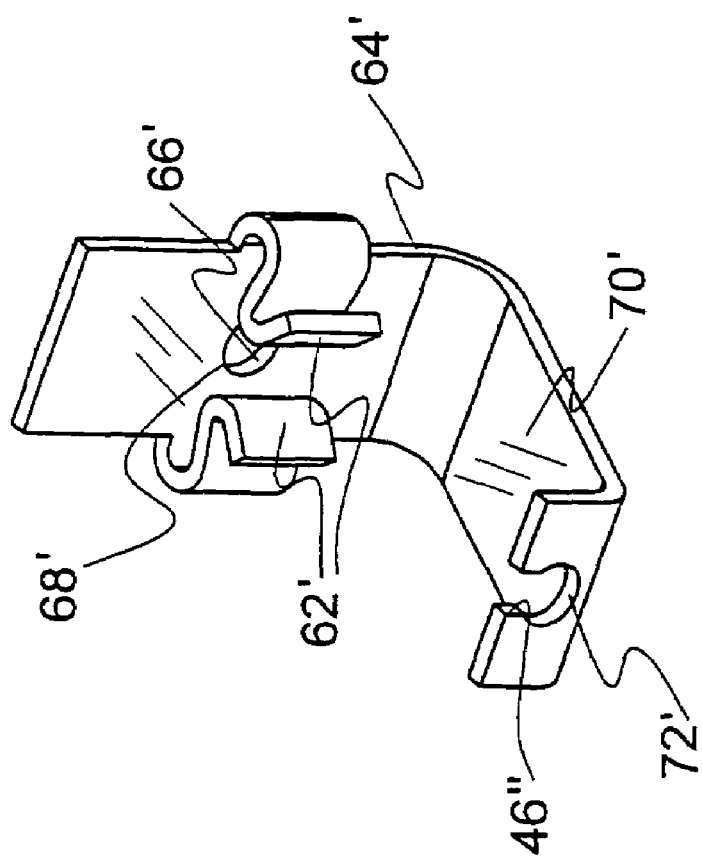
FIG. 27 is a perspective view of the safety shield apparatus illustrated in FIG. 23 showing an alternate retainer embodiment, which includes a slot for permitting a guidewire to extend through the safety shield apparatus.
Figure 28:
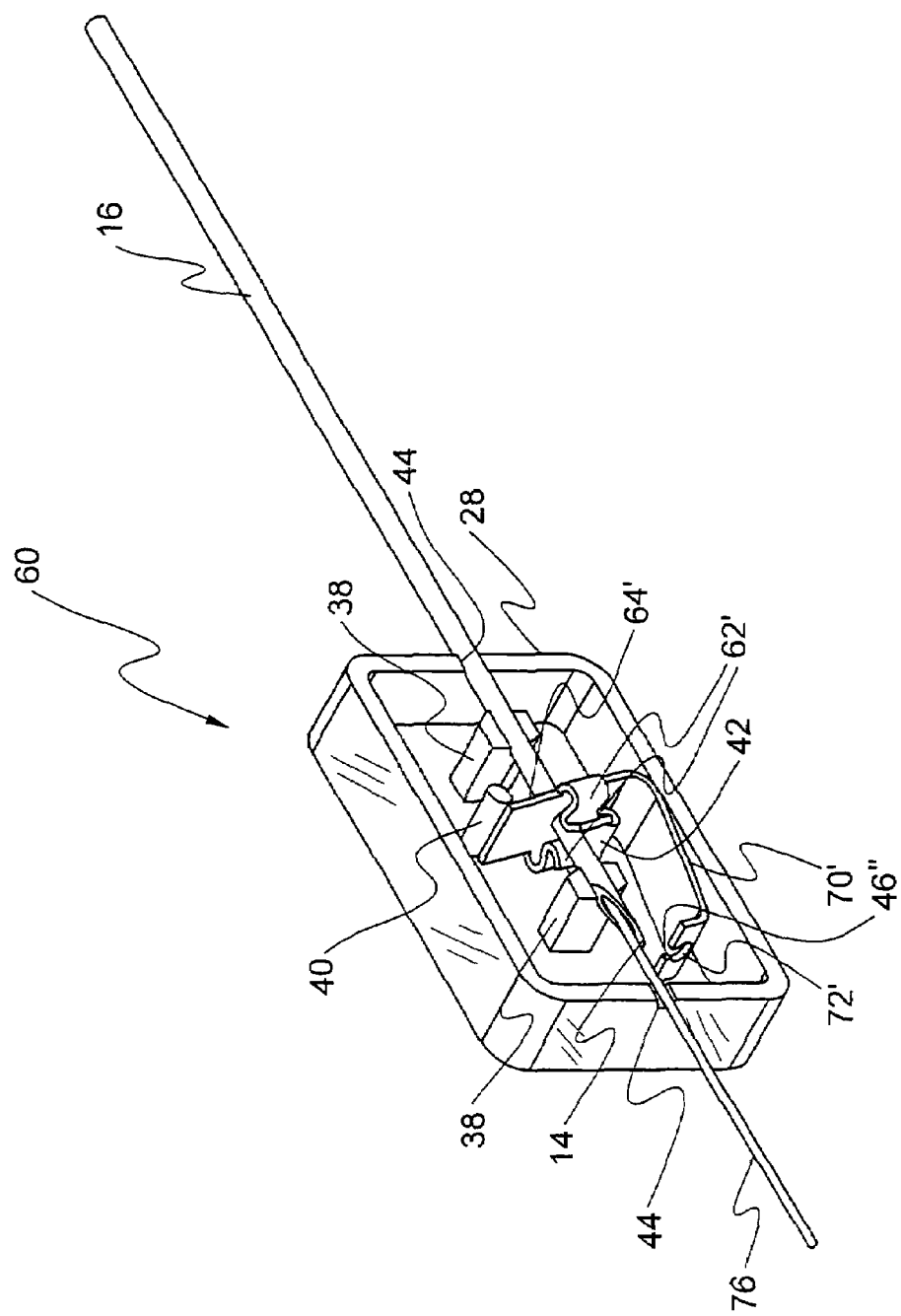

Safety shield 60 may also be adapted for use with a medical needle device having a guidewire 76, as shown in FIG. 28. An alternate embodiment of retainer 70 is shown in FIGS. 27 and 28, which includes a slot 46" for permitting a guidewire to extend through the safety shield 60. Similar to the binding member 64 shown in FIGS. 23-26, the binding member 64' includes an aperture 66' through which the needle 16 passes. The binding member 64' also has binding surfaces 68' for binding to a medical needle 16. A retainer 70' integral with the binding member 64' communicates with the needle 16 for temporarily retaining the binding surfaces 68' in a non-binding position relative to the needle 16.

Figure 29:
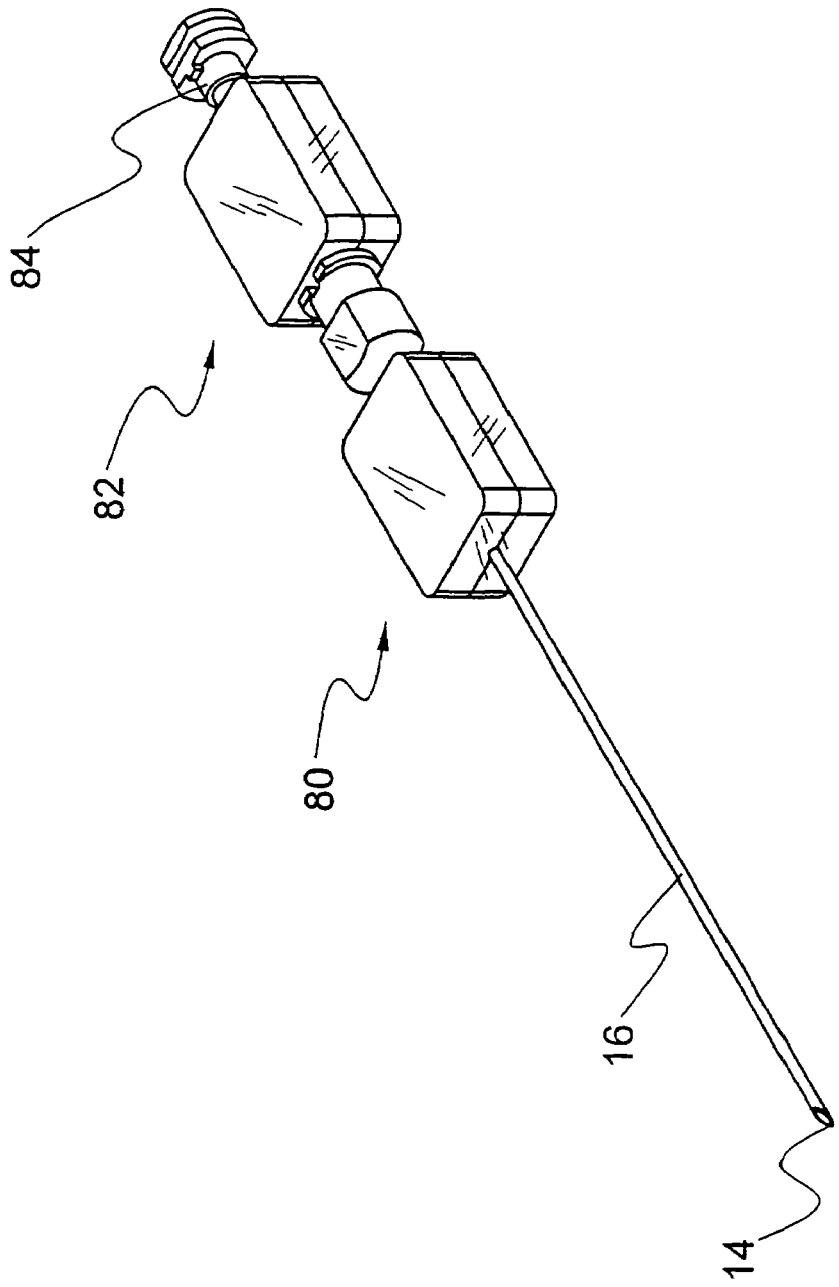
FIG. 29 is a perspective view of a safety shield apparatus having a second shield for protecting a distal end of a stylet passed through a bore of the needle.
Figure 30:
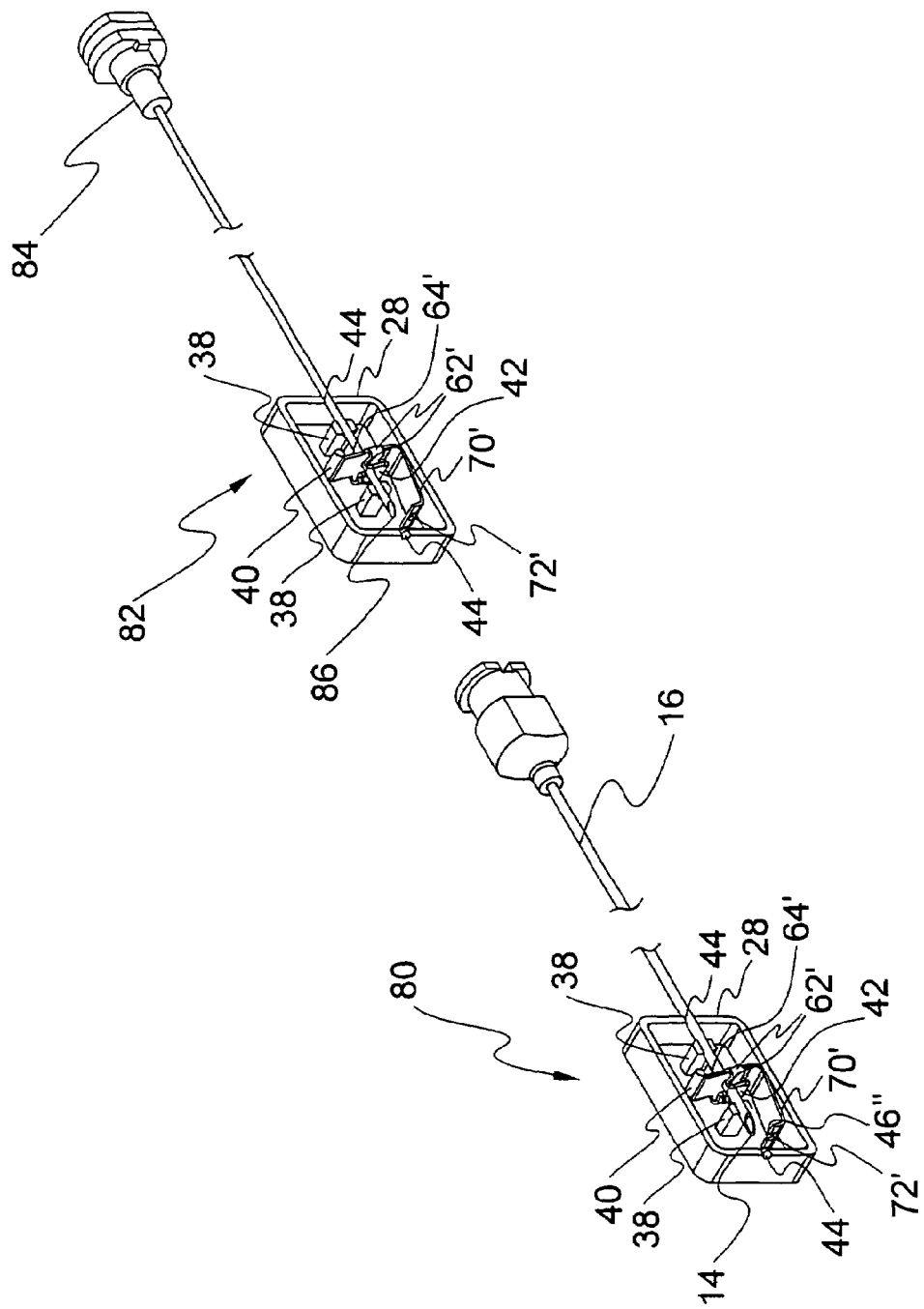
FIG. 30 is a perspective view of the safety shield apparatus shown in FIG. 29 with the first shield protecting the distal end of a needle and the second shield protecting the distal end of a stylet after use.

It is contemplated that the present invention may include multiple safety shields for protecting the needle 16 and a stylet 84 or other element passed through a bore of the needle 16. FIG. 29 is a perspective view of a safety shield apparatus having a first safety shield assembly 80 and a second safety shield assembly 82 for protecting a distal end 86 of a stylet 84 passed through a bore of the needle 16. FIG. 30 is a perspective view of the first and second safety shield assemblies 80 and 82, respectively, after actuation protecting the distal end 14 of a needle 16 and the distal end 86 of a stylet 84 after use. First and second safety shields 80 and 82 illustrated in FIG. 30 are similar to safety shield assembly 60 shown in FIG. 28. However, any of the above described safety shield assemblies may be utilized.

The invention of the present disclosure may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A medical needle shield apparatus comprising:
   a shield slidably movable along a medical needle from a proximal position where a distal end of the needle is exposed, to a distal position where the shield protects the distal end of the needle, said shield comprising:
   a binding member having an aperture through which the needle passes, said aperture having binding surfaces;
   a retainer integral with the binding member and in communication with the needle for temporarily retaining the binding surfaces in a non-binding position relative to the needle; and
   a positioning member including a friction element configured to engage the medical needle and generate a drag force to cause inclination of the binding member from a substantially transverse position relative to an axial path defined by the needle for positioning the binding surfaces to secure the shield to the needle when a portion of the retainer in contact with the needle is advanced past the distal end of the needle and allows the retainer to release from the needle.

2. A medical needle shield apparatus as recited in claim 1, further comprising a housing for enclosing the shield, wherein the housing includes openings for the needle to pass through.

3. A medical needle shield apparatus as recited in claim 2, wherein the housing further comprises first and second blocking members for urging the binding member into a binding orientation.

4. A medical needle shield apparatus as recited in claim 1, wherein the positioning member comprises a unitary friction element disposed on the medical needle.

5. A medical needle shield apparatus as recited in claim 4, wherein the unitary friction element includes first and second surfaces for inclining the binding member and the binding member aperture is disposed between the first and second surfaces.

6. A medical needle shield apparatus as recited in claim 1, wherein the positioning member comprises a plurality of friction elements disposed on the medical needle.

7. A medical needle shield apparatus as recited in claim 1, wherein the friction element is integral to the binding member.

8. A medical needle shield apparatus as recited in claim 1, wherein the portion on the retainer in contact with the needle further includes a slot extending therefrom.

9. A medical needle shield apparatus as recited in claim 1, further comprising a second shield for protecting a distal end of a stylet or other element passed through a bore of the needle.

10. A medical needle shield apparatus comprising:
    a shield slidably movable along a medical needle from a proximal position where a distal end of the needle is exposed, to a distal position where the shield protects the distal end of the needle, said shield comprising:
    a binding member having an aperture through which the needle passes, said aperture having binding surfaces;

a retainer integral with the binding member and in communication with the needle for temporarily retaining the binding surfaces in a non-binding position relative to the needle;

a positioning member including a friction element configured to engage the medical needle and generate a drag force to cause inclination of the binding member from a substantially transverse position relative to an axial path defined by the needle for positioning the binding surfaces to secure the shield to the needle when a portion of the retainer in contact with the needle is advanced past the distal end of the needle and allows the retainer to release from the needle; and a housing for enclosing the shield, wherein the housing includes openings for the needle to pass through.

11. A medical needle shield apparatus as recited in claim 10, wherein the positioning member comprises a plurality of friction elements disposed on the medical needle.

12. A medical needle shield apparatus as recited in claim 11, wherein the plurality of friction elements are integral to the binding member.

13. A medical needle shield apparatus as recited in claim 10, wherein the positioning member comprises a unitary friction element disposed on the medical needle.

14. A medical needle shield apparatus as recited in claim 13, wherein the unitary friction element includes first and second surfaces for inclining the binding member and the binding member aperture is disposed between the first and second surfaces.

15. A medical needle shield apparatus as recited in claim 10, wherein the housing further comprises first and second blocking members for urging the binding member into a binding orientation.

16. A medical needle shield apparatus as recited in claim 10, wherein the portion on the retainer in contact with the needle further includes a slot extending therefrom.

17. A medical needle shield apparatus as recited in claim 10, further comprising a second shield for protecting a distal end of a stylet or other element passed through a bore of the needle.

18. A medical needle shield apparatus comprising:
a shield slidably movable along a medical needle from a proximal position where a distal end of the needle is exposed, to a distal position where the shield protects the distal end of the needle, said shield comprising:
a binding member having an aperture through which the needle passes, said aperture having binding surfaces;
a retainer integral with the binding member and in communication with the needle for temporarily retaining the binding surfaces in a non-binding position relative to the needle; and
one or more friction elements configured to engage the medical needle and generate a drag force to cause inclination of the binding member from a substantially transverse position relative to an axial path defined by the needle for positioning the binding surfaces to secure the shield to the needle when a portion of the retainer in contact with the needle is advanced past the distal end of the needle and allows the retainer to release from the needle.

19. A medical needle shield apparatus as recited in claim 18, further comprising a housing for enclosing the shield, wherein the housing includes openings for the needle to pass through.

20. A medical needle shield apparatus comprising:
a shield slidably movable along a medical needle from a proximal position where a distal end of the needle is exposed, to a distal position where the shield protects the distal end of the needle, said shield comprising:
a binding member having an aperture through which the needle passes, said aperture having binding surfaces;
a retainer integral with the binding member and in communication with the needle for temporarily retaining the binding surfaces in a non-binding position relative to the needle; and
one or more friction elements integral with the binding member and configured to engage the medical needle and generate a drag force to cause inclination of the binding member from a substantially transverse position relative to an axial path defined by the needle for positioning the binding surfaces to secure the shield to the needle when a portion of the retainer in contact with the needle is advanced past the distal end of the needle and allows the retainer to release from the needle.

21. A medical needle shield apparatus as recited in claim 20, further comprising a housing for enclosing the shield, wherein the housing includes openings for the needle to pass through.

22. A medical needle shield apparatus as recited in claim 20, further comprising a second shield for protecting a distal end of a stylet or other element passed through a bore of the needle.

23. A medical needle shield apparatus comprising:
a shield slidably movable along a medical needle from a proximal position where a distal end of the needle is exposed, to a distal position where the shield protects the distal end of the needle, said shield comprising:
a binding member having an aperture through which the needle passes, said aperture having binding surfaces;
a retainer integral with the binding member and in communication with the needle for temporarily retaining the binding surfaces in a non-binding position relative to the needle; and
a unitary friction element disposed on the needle and having first and second surfaces disposed fore and aft of the binding member aperture for inclining the binding member from a substantially transverse position relative to an axial path defined by the needle and positioning the binding surfaces to secure the shield to the needle when a portion of the retainer in contact with the needle is advanced past the distal end of the needle and allows the retainer to release from the needle.

24. A medical needle shield apparatus as recited in claim 23, further comprising a housing for enclosing the shield, wherein the housing includes openings for the needle to pass through.

25. A medical needle shield apparatus as recited in claim 23, further comprising a second shield for protecting a distal end of a stylet or other element passed through a bore of the needle.

26. A medical needle shield apparatus comprising:
a shield slidably movable along a medical needle from a proximal position where a distal end of the needle is exposed, to a distal position where the shield protects the distal end of the needle, said shield comprising:
a binding member having an aperture through which the needle passes, said aperture having binding surfaces;
a retainer integral with the binding member and in communication with the needle for temporarily retaining the binding surfaces in a non-binding position relative to the needle; and
a positioning member integral with the binding member, wherein the positioning member pushes against the needle and the binding member inclines from a substantially transverse position relative to an axial path defined by the needle at least primarily by the pushing of the positioning member when a portion of the retainer in contact with the needle is advanced past the distal end of the needle to enable the binding surfaces to secure the shield to the needle.

27. A medical needle shield apparatus as recited in claim 26, further comprising a housing for enclosing the shield, wherein the housing includes openings for the needle to pass through.

28. A medical needle shield apparatus as recited in claim 27, wherein the positioning member is configured to push against the needle without pushing against the perimeter of the housing.

29. A medical needle shield apparatus as recited in claim 27, wherein the housing further comprises at least one blocking member for urging the binding member into a binding orientation.

30. A medical needle shield apparatus as recited in claim 29, wherein the housing further comprises at least one needle support positioned above the needle and at least one needle support below the needle for guiding the needle through the shield.

* * * * *

UNITED STATES PATENT AND TRADEMARK OFFICE
CERTIFICATE OF CORRECTION

PATENT NO. : 7,611,485 B2
APPLICATION NO. : 10/919983
DATED : November 3, 2009
INVENTOR(S) : F. Mark Ferguson It is certified that error appears in the above-identified patent and that said Letters Patent is hereby corrected as shown below:

On the title page, (73) Assignee, replace:

"C. R. Bard, Inc., Murray Hill, NJ (US)"

with:

--Specialized Health Products, Inc., Salt Lake City, UT (US)--

Signed and Sealed this

Eighth Day of December, 2009

David J. Kappos
*Director of the United States Patent and Trademark Office*